(12) United States Patent
Wisbey et al.

(10) Patent No.: US 10,292,606 B2
(45) Date of Patent: May 21, 2019

(54) SYSTEM AND METHOD FOR DETERMINING PERFORMANCE CAPACITY

(71) Applicant: LOGITECH EUROPE, S.A., Lausanne (CH)

(72) Inventors: Ben Wisbey, Canberra (AU); Hagen Diesterbeck, Coromandel (NZ); David Shepherd, Canberra (AU)

(73) Assignee: Logitech Europe, S.A., Lausanne (CH)

( * ) Notice: Subject to any disclaimer, the term of this patent is extended or adjusted under 35 U.S.C. 154(b) by 548 days.

(21) Appl. No.: 14/934,101

(22) Filed: Nov. 5, 2015

(65) Prior Publication Data
US 2017/0127957 A1     May 11, 2017

(51) Int. Cl.
| | |
|---|---|
| A61B 5/024 | (2006.01) |
| A61B 5/11 | (2006.01) |
| A61B 5/00 | (2006.01) |
| A61B 5/0205 | (2006.01) |

(52) U.S. Cl.
CPC ........ *A61B 5/02405* (2013.01); *A61B 5/0205* (2013.01); *A61B 5/02427* (2013.01); *A61B 5/1118* (2013.01); *A61B 5/6803* (2013.01); *A61B 5/02438* (2013.01); *A61B 2505/09* (2013.01)

(58) Field of Classification Search
CPC . A61B 5/02405; A61B 5/6803; A61B 5/1118; A61B 5/02427; A61B 5/0205
See application file for complete search history.

(56) References Cited

U.S. PATENT DOCUMENTS

| | | |
|---|---|---|
| 2,189,096 A | 2/1940 | Alonge |
| 3,543,724 A | 12/1970 | Kirkpatrick et al. |
| 3,978,849 A | 9/1976 | Geneen |
| 4,129,124 A | 12/1978 | Thalmann |
| 4,224,984 A | 9/1980 | Cramer et al. |
| 4,307,727 A | 12/1981 | Haynes |
| 4,331,154 A | 5/1982 | Broadwater et al. |

(Continued)

OTHER PUBLICATIONS

"Elite Clock Military Style LED Watch" by ledwatchsuk. YouTube [dated May 31, 2011][online][retrieved on Aug. 14, 2015].

(Continued)

*Primary Examiner* — Mark Bockelman
(74) *Attorney, Agent, or Firm* — Patterson & Sheridan, LLP

(57) ABSTRACT

Systems and methods are provided for determining performance capacity. One such system includes a wearable device having a biosensor that measures biometrics and a motion sensor that monitors activity. The system also includes a processor coupled to the biosensor and the motion sensor, and a non-transitory computer-readable medium operatively coupled to the processor and storing instructions that, when executed, cause the processor to execute specific functions. The instructions are executed to cause the processor to generate biometric data from the biometrics and activity data from the activity. Further, the instructions are executed to create a response profile based on one or more of a heart rate variability (HRV) score based on the biometric data, a fatigue score based on the activity data, a predicted HRV score based on the biometric and activity data, and a predicted fatigue score based on the biometric data and/or the activity data.

9 Claims, 19 Drawing Sheets

(56) References Cited

U.S. PATENT DOCUMENTS

| | | |
|---|---|---|
| 4,407,295 A | 10/1983 | Steuer et al. |
| 4,409,983 A | 10/1983 | Albert |
| 4,491,970 A | 1/1985 | Lawhite et al. |
| 5,301,154 A | 4/1994 | Suga |
| 5,392,261 A | 2/1995 | Hsu |
| 5,406,952 A | 4/1995 | Barnes et al. |
| 5,524,637 A | 6/1996 | Erickson |
| 5,734,625 A | 3/1998 | Kondo |
| 5,755,623 A | 5/1998 | Mizenko |
| 5,899,370 A | 5/1999 | Bould |
| 6,151,968 A | 11/2000 | Chou |
| 6,361,503 B1 | 3/2002 | Starobin et al. |
| 6,736,759 B1 | 5/2004 | Stubbs et al. |
| 7,192,401 B2 | 3/2007 | Saalasti et al. |
| 7,717,827 B2 | 5/2010 | Kurunmaki et al. |
| 7,914,425 B2 | 3/2011 | Hanoun |
| 8,992,385 B2 | 3/2015 | Lemos |
| 2002/0151811 A1 | 10/2002 | Starobin et al. |
| 2002/0188210 A1 | 12/2002 | Aizawa |
| 2003/0065269 A1 | 4/2003 | Vetter et al. |
| 2005/0056655 A1 | 3/2005 | Gary |
| 2005/0116811 A1 | 6/2005 | Eros et al. |
| 2005/0256416 A1 | 11/2005 | Chen |
| 2006/0183980 A1 | 8/2006 | Yang |
| 2007/0118043 A1 | 5/2007 | Oliver et al. |
| 2008/0132383 A1 | 6/2008 | Einav et al. |
| 2008/0228089 A1 | 9/2008 | Cho et al. |
| 2009/0312656 A1 | 12/2009 | Lau et al. |
| 2010/0197463 A1 | 8/2010 | Gilley et al. |
| 2011/0021319 A1 | 1/2011 | Nissila et al. |
| 2011/0092790 A1 | 4/2011 | Wilder-Smith et al. |
| 2011/0260870 A1 | 10/2011 | Bailey |
| 2012/0022341 A1 | 1/2012 | Zdeblick |
| 2012/0168471 A1 | 7/2012 | Wilson |
| 2012/0184871 A1* | 7/2012 | Jang ............... A61B 5/1108 600/546 |
| 2012/0253485 A1 | 10/2012 | Weast et al. |
| 2013/0064049 A1 | 3/2013 | Pileri et al. |
| 2013/0237778 A1 | 9/2013 | Rouquette |
| 2014/0032234 A1 | 1/2014 | Anderson |
| 2014/0073486 A1 | 3/2014 | Ahmed et al. |
| 2014/0107493 A1 | 4/2014 | Yuen et al. |
| 2014/0228175 A1 | 8/2014 | Lemos et al. |

OTHER PUBLICATIONS

"Watch Stylish Blue Light LED Round Dial Matrix Stainless from ChinaBuye.com" by YnopoB. Youtube [dated Apr. 23, 2012][online][retrieved on Dec. 31, 2015] (https://www.youtube.com/watch?v=e_LWbXHvvWg).

\* cited by examiner

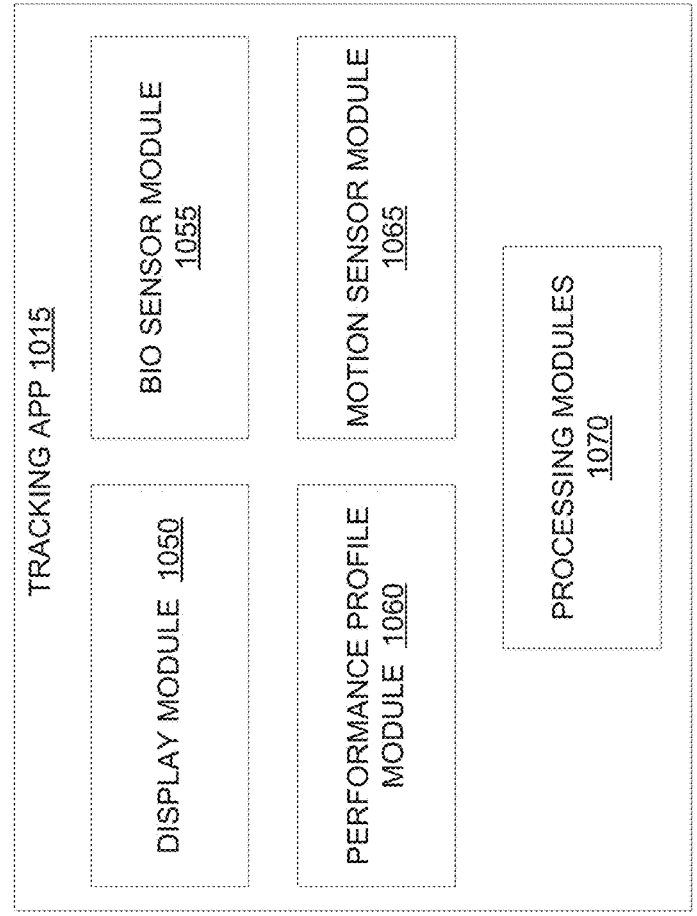
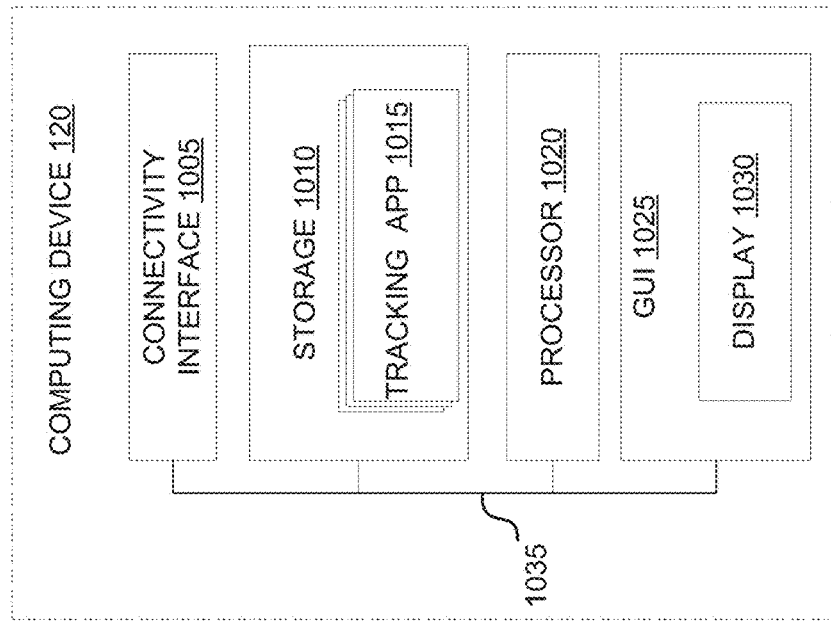
FIG. 10B
FIG. 10A

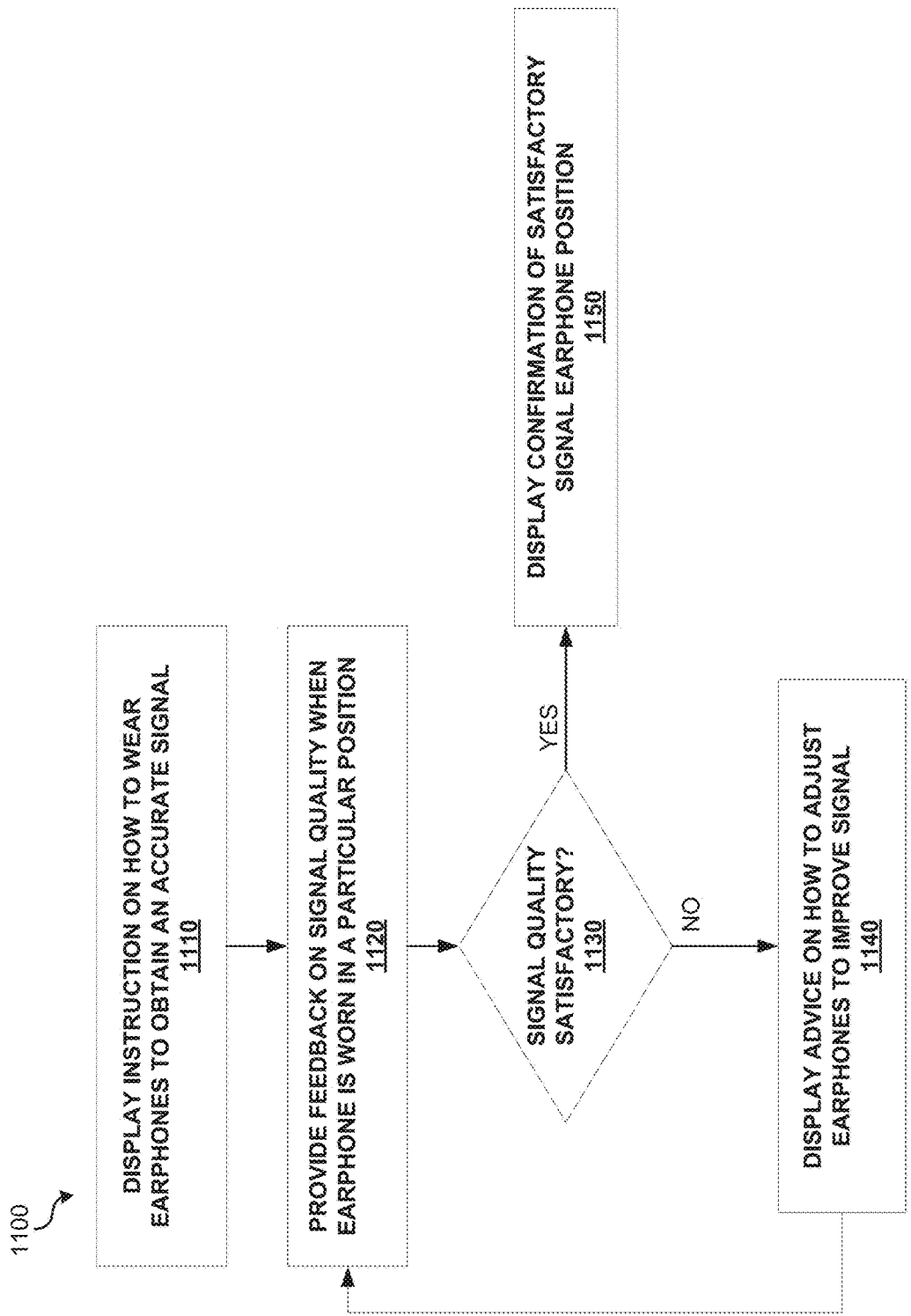

SYSTEM AND METHOD FOR DETERMINING PERFORMANCE CAPACITY

TECHNICAL FIELD

The present disclosure relates generally to fitness and activity monitoring devices. More particularly, the present disclosure is directed to systems, methods, and devices, for determining a user's performance capacity.

BACKGROUND

Currently available fitness monitoring devices monitor and track a user's fitness level, for example, by counting the user's steps, total calories burned, miles run, etc., and by monitoring the user's heart rate. Currently available solutions also may seek to determine a proper training load for a user based on universal statistics regarding the user's physical and/or biological characteristics, where such universal statistics attempt to gauge the user's likely response to a given training load. Nevertheless, currently available fitness monitoring devices do not provide modeling performance capabilities or capacities that enable specific prediction of a user's response to activity, rest, and other scenarios, and use the response to determine a training load based on the user's performance capacity reflected by the predicted response. Rather, current solutions are limited to merely tracking a user's activity and response to the same, and thus do not provide training loads that holistically maximize the user's performance capacity in a balanced way, nor do they provide the ability to meaningfully compare different potential training loads, hence do not provide the user with the user's best overall fitness and well-being.

SUMMARY

In view of the above shortcomings in conventional fitness monitoring devices, there exists a need for determining performance capacity of a user that takes into account one or more of biometric data and activity data. In particular, there exists a need for fitness monitoring devices that enable modeling a user's response to the user's activity, as well as to other events and circumstances that affect the user's fitness and/or well-being, in order to intelligently and accurately calculate the user's predicted response to a training load. In this manner, the user can implement a training load that will allow the user to obtain a higher level of fitness, balance, and health. In this connection, embodiments of the present disclosure include systems, methods, and devices, capable of determining performance capacity of a user, including, for example, using a combination of biosensors and motion sensors, as well as wirelessly connected processors and/or computing devices.

Embodiments of the present disclosure include a system for determining performance capacity. The system includes a wearable device, which in turn includes a biosensor that measures biometrics and a motion sensor that monitors activity. In embodiments of the system for determining performance capacity, the wearable device includes earphones and/or a band. In embodiments of the system, the biosensor includes finger and wrist biosensors or an optical heartrate sensor.

The system also includes a processor coupled to the biosensor and the motion sensor. The processor is configured to process electronic signals generated by the biosensor and the motion sensor. Additionally, the system includes a non-transitory computer-readable medium operatively coupled to the processor and storing instructions that, when executed, cause the processor to perform various functions. One such function is to generate biometric data from the biometrics measured by the biosensor. Another such function is to generate activity data from the activity monitored by the motion sensor. Yet another such function is to create a response profile based on one or more of a heart rate variability (HRV) score based on the biometric data, a fatigue score based on the activity data, a predicted HRV score based on the biometric data and the activity data, and a predicted fatigue score based on one or more of the biometric data and the activity data.

In example implementations of the system for determining performance capacity, the non-transitory computer-readable medium further stores instructions that, when executed, cause the processor to perform additional functions. One such function is to determine a fatigue value based on the combination of a previous fatigue value with a first difference calculated by the processor. The first difference is between a previous activity value and the previous fatigue value. The first difference is scaled by a fatigue decay, and the previous activity value is derived from the activity data. Another such function is to calculate an average fatigue value based on a set of the fatigue values previously determined. Yet another such function is to calculate a fatigue value variation based on the set of the fatigue values previously determined. Another such function is to calculate the fatigue score based on a second difference calculated by the processor. The second difference is between the average fatigue value and the fatigue value, and the second difference is scaled by the fatigue value variation.

In additional example implementations of the system, the non-transitory computer-readable medium further stores instructions that, when executed, cause the processor to further functions. One such function is to maintain, for a previous measuring period, an aggregation of the calculated fatigue scores and an aggregation of the activity data. Another such function is to create a fatigue model derived from a correlation of the aggregation of calculated fatigue scores with the aggregation of the activity data. Yet another such function is to use the fatigue model to generate the predicted fatigue score based the activity data.

The system for determining performance capacity, in example deployments of the present disclosure, includes circuits that receive and process electrical signals from the biosensor. In some such deployments, the non-transitory computer-readable medium further stores instructions that, when executed, cause the processor to perform various functions. The processor generates the biometric data based on the electrical signals as processed by the circuits. Also, the processor calculates a current HRV value from the biometric data, and an average HRV value based on a set of HRV values previously calculated. Furthermore, the processor calculates variation in the HRV value based on the set of the HRV values previously calculated. The processor also calculates the HRV score based on a difference between the average HRV value and the current HRV value. The difference is scaled by the variation in the HRV value.

In additional example deployments, the non-transitory computer-readable medium further stores instructions that, when executed, cause the processor to perform additional functions. In such deployments, the processor maintains, for a previous measuring period, an aggregation of the calculated HRV scores and an aggregation of the activity data. Furthermore, the processor creates an HRV model derived from a correlation of the aggregation of the calculated HRV scores with the aggregation of the activity data. Also, the processor uses the HRV model to generate the predicted HRV score based on the activity data.

Embodiments of the present disclosure also include a computer-implemented method for determining performance capacity. The method includes measuring biometrics using a biosensor embedded in a wearable device. The method also includes generating biometric data from the biometrics. Also, the method includes monitoring activity using a motion sensor embedded in the wearable device. The method further includes generating activity data from the activity. Moreover, the method includes creating a response profile based on one or more a heart rate variability (HRV) score based on the biometric data, a fatigue score based on the activity data, a predicted HRV score based on the biometric data and the activity data, and a predicted fatigue score based on one or more of the biometric data and the activity data.

In example embodiments of the computer-implemented method, the computer-implemented method, creating the response profile includes various operations. In such embodiments, creating the response profile includes determining a fatigue value based on the combination of a previous fatigue value with a first difference calculated by a processor. The first difference is between the previous activity value and the previous fatigue value. The first difference is scaled by a fatigue decay. Creating the response profile also includes calculating, based on a set of the fatigue values previously determined, an average fatigue value and a variation in the fatigue value. Further, creating the response profile includes calculating the fatigue score based on a second difference. The second difference is between the average fatigue value and the fatigue value. The second difference is scaled by the variation in the fatigue value.

In additional example embodiments of the computer-implemented method, creating the response profile includes maintaining, for a previous measuring period, an aggregation of the calculated fatigue scores and an aggregation of the activity data. Creating the response profile also includes creating a fatigue model derived from a correlation of the aggregation of the calculated fatigue scores with the aggregation of the activity data. In addition, creating the response profile includes using the fatigue model to generate the predicted fatigue score.

Creating the response profile may also include calculating a current HRV value from the biometric data. Further, creating the response profile may include calculating, based on a set of HRV values previously calculated using the biometric data, an average HRV value and an HRV variation. Further still, creating the response profile may include calculating the HRV score based on a difference between the average HRV value and the current HRV value. The difference is scaled by the HRV variation.

In potential implementations of the computer-implemented method, creating the response profile includes additional operations. In such implementations, creating the response profile includes creating an HRV model based on a correlation of calculated HRV scores with the activity data. Further, creating the response profile includes using the HRV model to generate the predicted HRV score based on the activity data. In additional instances, creating the response profile includes generating a scaled predicted HRV score from the predicted HRV score. Furthermore, creating the response profile includes generating a scaled fatigue score from the fatigue score. In addition, creating the response profile includes combining the scaled predicted HRV score and the scaled fatigue score. In addition example deployments of the present disclosure of the computer-implemented method, creating the response profile includes generating a scaled HRV score from the HRV score. Further, creating the response profile includes generating a scaled fatigue score from the fatigue score, and combining the scaled HRV score and the scaled fatigue score.

As mentioned above, embodiments of the present disclosure include systems for determining performance capacity. One example of such a system includes a wireless receiver that receives biometric data and activity data. The biometric data is indicative of biometrics measured by a biosensor. The activity data is indicative of activity monitored by a motion sensor. The system also includes a processor coupled to the wireless receiver. Further, the system includes a non-transitory computer-readable medium operatively coupled to the processor and storing instructions that, when executed, cause the processor to perform various functions. Based on the stored instructions, the processor creates a response profile based on one or more of a heart rate variability (HRV) score that is based on the biometric data, a fatigue score that is based on the activity data, a predicted HRV score that is based on the biometric data and the activity data, and a predicted fatigue score that is based on one or more of the biometric data and the activity data.

In example deployments of the above-mentioned system, a wearable device is included. The wearable device includes the biosensor and the motion sensor. The biosensor generates electrical signals indicative of the biometrics, and the motion sensor generates electrical signals indicative of the activity. The wearable device also includes circuits that receive and process the electrical signals from the biosensor and the motion sensor to generate the biometric data and the activity data. Additionally, the wearable device includes a transmitter that transmits the biometric data and the activity data from the wearable device to the wireless receiver. The wearable device may include earphones and/or a wristband. The biosensor may include finger and/or wrist biosensors and/or an optical heartrate sensor.

In additional embodiments of the system, the non-transitory computer-readable medium further stores instructions that, when executed, cause the processor to perform further functions. One such function is that the processor scales the predicted HRV score by a first scaling factor to generate a scaled predicted HRV score. Another such function is that the processor scales the fatigue score by a second scaling factor to generate a scaled fatigue score. Yet another such function is that the processor creates the response profile based on the combination of the scaled predicted HRV score and the scaled fatigue score.

In yet additional embodiments of the system for determining performance capacity, the non-transitory computer-readable medium further stores instructions that, when executed, cause the processor to further functions. In such embodiments, the processor scales the HRV score by a first scaling factor to generate a scaled HRV score. The processor also scales the fatigue score by a second scaling factor to generate a scaled fatigue score. And the processor creates the response profile based on the combination of the scaled HRV score and the scaled fatigue score.

BRIEF DESCRIPTION OF THE DRAWINGS

Further aspects of the present disclosure will be more readily appreciated upon review of the detailed description of the various disclosed embodiments, described below, when taken in conjunction with the accompanying figures.

FIG. 10A is a block diagram of an example computing device that may be used to implement embodiments of the disclosure.

FIG. 10B illustrates an example application and modules according to embodiments of the present disclosure.

FIG. 11 is an example operational flow diagram illustrating various operations that may be performed to prompt a user to adjust the placement of earphones in the user's ear in accordance with various embodiments described herein.

The figures are described in greater detail in the description and examples below, are provided for purposes of illustration only, and merely depict typical or example embodiments of the disclosure. The figures are not intended to be exhaustive or to limit the disclosure to the precise form disclosed. It should also be understood that the disclosure may be practiced with modification or alteration, and that the disclosure may be limited only by the claims and the equivalents thereof.

DETAILED DESCRIPTION

Embodiments of the present disclosure are directed to systems, methods, and devices, capable of determining a user's performance capacity, including, e.g., the response that a user is likely to have to a given training load. The determination of the user's performance capacity is, in various deployments, based on biometric and activity data gathered from sensors that may be worn by the user, and may also be based on models created specifically for the user. The details of some example embodiments of the systems, methods, and devices of the present disclosure are set forth in the description below. Other features, objects, and advantages of the disclosure will be apparent to one of skill in the art upon examination of the present description, figures, examples, and claims. It is intended that all such additional systems, methods, features, and advantages be included within this description, be within the scope of the present disclosure, and be protected by one or more of the accompanying claims.

Figure 1:
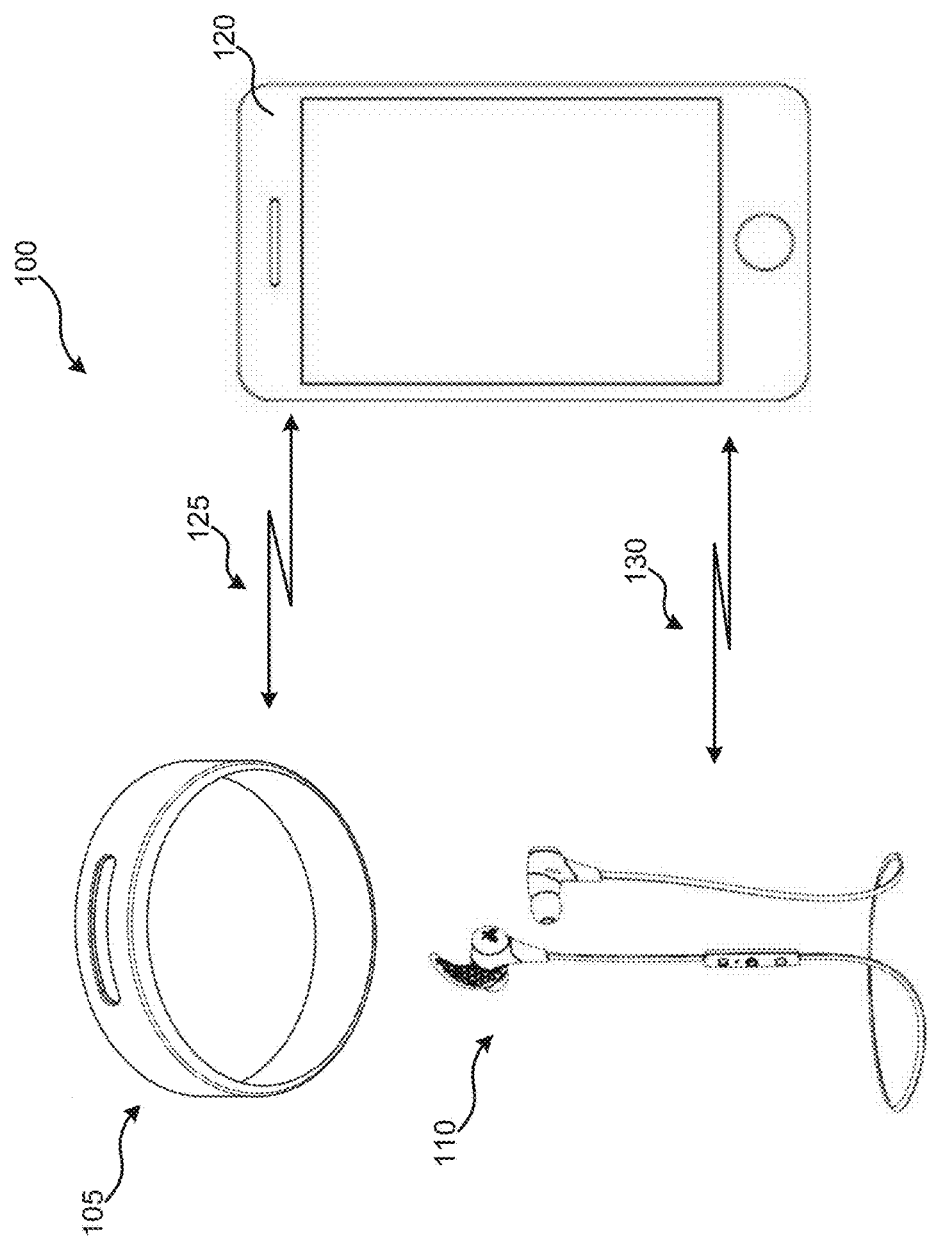
FIG. 1 illustrates an example communications environment in which embodiments of the disclosure may be implemented.

FIG. 1 depicts example communications environment 100, which may be used in connection with implementing embodiments of the disclosed systems, methods, and devices. As shown, communications environment 100 may include band 105 and earphones 110. As will be described in detail herein, band 105 and earphones 110 may be used to monitor activity and/or measure biometrics. Additionally, band 105 and earphones 110 may be coupled to computing device 120, which in the illustrated example is a mobile device. This coupling may be implemented in some examples using links 125 and 130, which in various instances may be a wired or wireless connection.

Computing device 120 may collect additional information from the user, such as biometrics and activity information that may be used to supplement or that may be used in place of information received from band 105 or earphones 110. Computing device 120 may include a variety of electronic computing devices, such as, for example, a smartphone, tablet, laptop, and the like. In such cases, computing device 120 may be configured to receive biometrics and/or activity information over links 125 and 130. Further, computing device 120 may include a graphical user interface (GUI) for displaying and interacting with one or more of band 105 and/or earphones 110, including by interacting with data collected by and received from band 105 and/or earphones 110, and by controlling the operation of band 105 and/or earphones 110.

Here it will be noted that the GUI of computing device 120 may additionally perform functions such as accepting user input and displaying processed biometric and activity data to the user. The GUI may be provided by various operating systems known in the art, such as, for example, iOS, Android, Windows Mobile, Windows, Mac OS, Chrome OS, Linux, Unix, a gaming platform OS (e.g., Xbox, PlayStation, Wii), etc. In various embodiments, links 125 and 130 may be based on one or more wireless communication protocols such as Bluetooth, ZigBee, 802.11 protocols, Infrared (IR), Radio Frequency (RF), 2G, 3G, 4G, etc.

Figure 2:
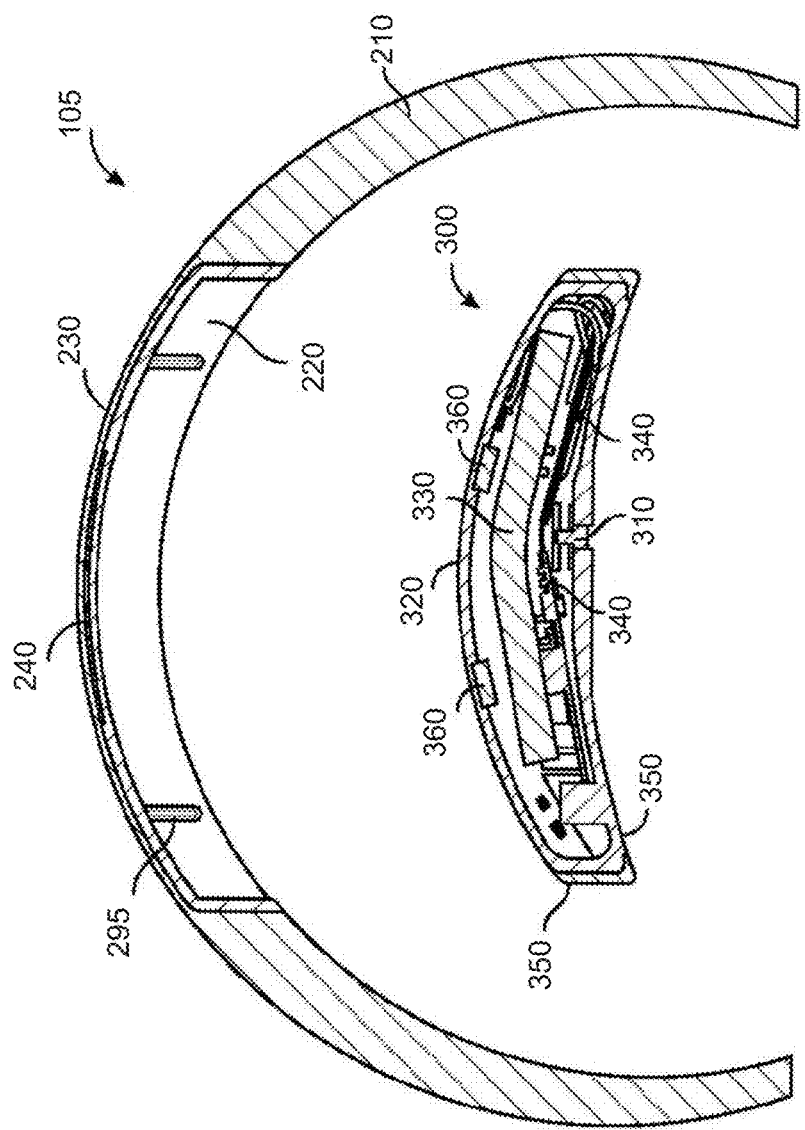
FIG. 2 illustrates a cross-sectional view of an example band that may be used to implement embodiments of the disclosure.
Figure 3:
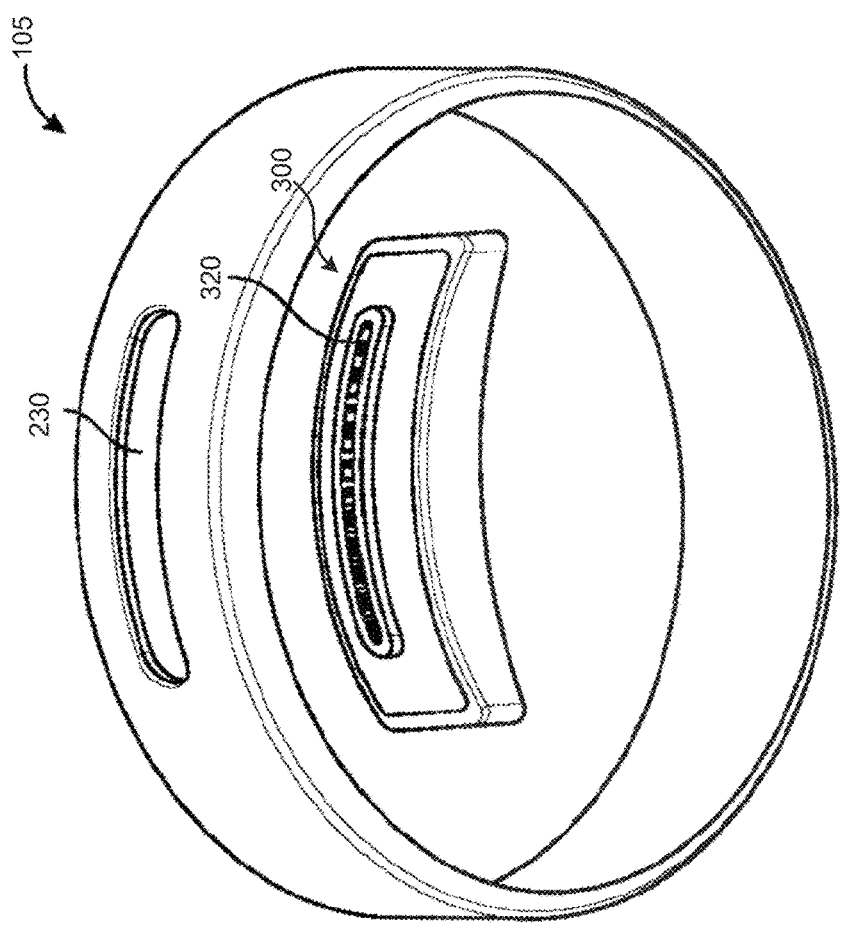
FIG. 3 illustrates a perspective view of the example band.

FIG. 2 depicts an exploded cross-sectional view of example embodiments of band 105. FIG. 3 illustrates a perspective view of band 105. Aspects of FIGS. 2 and 3 will now be described together. As depicted, band 105 includes band portion 210 and electronic capsule 300, which includes various electronic components embodied therein. Electronic capsule 300 is a removable/detachable component that may be coupled to and removable/detachable from band portion 210. This may be accomplished in a variety of ways, e.g., magnetic attraction forces, snap-fit/friction, etc. In other cases, electronic capsule 300 may be integrally formed with band portion 210.

Electronic capsule 300 may include various components, such as battery 330, logic circuits 340, casing 350, and one or more of wrist biosensor 310, finger biosensor 320, and/or a motion sensor (e.g., accelerometer, gyroscope, magnetometer, or other inertial measurement unit). Typically, at least one of wrist biosensor 310 and finger biosensor 320 is a heart rate sensor configured to detect the heart rate of a wearer of band 105. In the illustrated embodiment, finger biosensor 320 protrudes outwardly from a first side (i.e., the top) of casing 350, and wrist biosensor protrudes outwardly from a second side (i.e., the bottom) of casing 350. As depicted, aperture 230 of band portion 210 substantially matches the dimensional profile of finger biosensor 320, such that finger biosensor 320 may be exposed and accessible to the touch of a user's finger through aperture 230 when band 105 is worn by the user. In various embodiments, battery 330, logic circuits 340, and an optional motion sensor are enclosed inside of casing 350. Battery 330 is electronically coupled and supplies power to logic circuits 340. By way of example, logic circuits 340 may by implemented using printed circuit boards (PCBs). Although band 105 is shown in FIGS. 2 and 3 as including both wrist biosensor 310 and finger biosensor 320, some embodiments include only one or the other.

Casing 350 may be made of various materials known in the art, including, for example, molded plastic, silicone, rubber, or another moldable material. Additionally, casing 350 may be sealing using an ultrasonic welding process to be substantially water tight, thus protecting electronic capsule 300 from the elements. Further, band 105 may be configured to encircle (either partially as in FIG. 2, or entirely as in FIG. 3) a wrist or other limb (e.g., ankle, etc.) of a human or other animal or object. In one embodiment, band 105 is adjustable in size/fit. In some embodiments, cavity 220 is notched on the radially inward facing side of band 105 and shaped to substantially the same dimensions as the profile of electronic capsule 300. In addition, aperture 230 may be located in the material of band 105 within cavity 220. Aperture 230 may be shaped to substantially the same dimensions as the profile of the finger biosensor 320. As shown, cavity 220 and aperture 230 are in combination designed to detachably couple to electronic capsule 300 such that, when electronic capsule 300 is positioned inside cavity 220, finger biosensor 320 protrudes at least partially into aperture 230 such that electronic capsule 300 may be exposed to the touch of a user's finger. Electronic capsule 300 may further include one or more magnets 360 configured to secure electronic capsule 300 in cavity 220. Magnets 360 may be concealed in casing 350. Alternatively, cavity 220 may be configured to conceal magnets 360 when electronic capsule 300 detachably couples in cavity 220 and aperture 230.

Band 105 may further include a ferromagnetic metal strip 240 concealed in band portion 210 within cavity 220. In such a case, when electronic capsule 300 is positioned within cavity 220, magnets 360 are attracted to ferromagnetic metal strip 240 and pull electronic capsule 300 radially outward with respect to band portion 210. The force provided by magnets 360 may detachably secure electronic capsule 300 inside cavity 220. In alternative embodiments, electronic capsule 300 may be positioned inside cavity 220 and be affixed therein using a form-fit, press-fit, snap-fit, friction-fit, VELCRO, or other temporary adhesion or attachment technology.

In some embodiments, logic circuits 340 include an a motion sensor that includes an inertial measurement unit (e.g., one or more of a gyroscope, accelerometer, and magnetometer, etc.), a wireless transmitter, and additional circuitry. Logic circuits 340 may be configured to process electronic signals from biosensors (e.g., finger biosensor 320 and wrist biosensor 310) and/or motion sensors, convert/store the electronic signals as data, and output the data via the transmitter (e.g., using wireless protocols described herein). In other scenarios, this data may be output using a wired connection (e.g., USB, fiber optic, HDMI, or the like).

Referring again to electronic capsule 300, in some embodiments, the electronic signals processed by logic circuits 340 include an activation time signal and a recovery time signal. In these embodiments, logic circuits 340 may process the electronic signals to calculate an activation recovery interval equal to the difference between the activation time signal and the recovery time signal. The electronic of signals may include heart rate information collected by and received from one or more of the wrist biosensor 310 and finger biosensor 320. Further still the electronic signals may include electro-cardio signals from a user's heart. In these embodiments, logic circuits 340 may process the electro-cardio signals to calculate and store a RR-interval and determine a heart rate. The RR-interval may be the delta in time between two R-waves, where the R-waves are the electro-cardio signals generated by a ventricle contraction in the heart. The RR-interval may further be used to calculate and store a heart rate variability (HRV) value that indicates the variation over time of the time delta between consecutive heartbeats. In some embodiments, logic circuits 340 may convey the electronic signals to, e.g., computing device 120, by a transmitter, such that computing device 120 may perform various calculations (e.g., of HRV).

In some instances, finger biosensor 320 and wrist biosensor 310 may be replaced or supplemented by a single biosensor configured to detect and measure biometric information. The single biosensor may be an optical biosensor such as a pulse oximeter configured to detect blood oxygen saturation levels. The pulse oximeter may output an electronic signal to logic circuits 340 indicating a detected cardiac cycle phase and/or heart rate, and logic circuits 340 may use such information (e.g. the cardiac cycle phase data) to further calculate an HRV value, or logic circuits 340 may convey the information to, e.g., computing device 120, by a transmitter, such that computing device 120 may perform various calculations (e.g., of HRV). Logic circuits 340, in some deployments, may further detect and store metrics based on motion detection, such as the amount of physical activity, sleep, or rest, over a period of time, or the amount of time with or without physical activity over a period of time.

Figure 4:
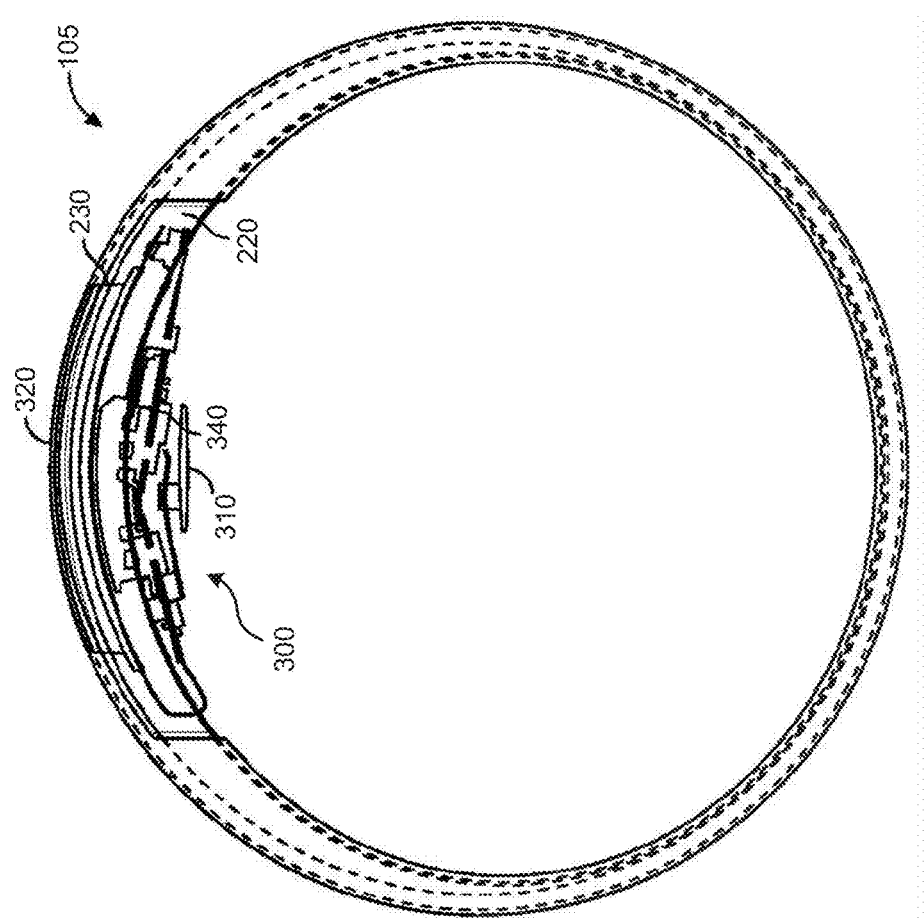
FIG. 4 illustrates a cross-sectional view of an example electronic capsule the may be used in connection with the example band, in accordance with various embodiments.

FIG. 4 illustrates a cross-sectional view of one embodiment of band 105 when assembled with electronic capsule 300. In this embodiment, electronic capsule 300 is positioned inside cavity 220 such that finger biosensor 320 is partially disposed in and exposed through aperture 230. Wrist biosensor 310 protrudes from the radially inward facing side band portion 210. In this configuration, wrist biosensor 310 may contact the skin on the wearer's limb when the band 105 is worn.

Figure 5:
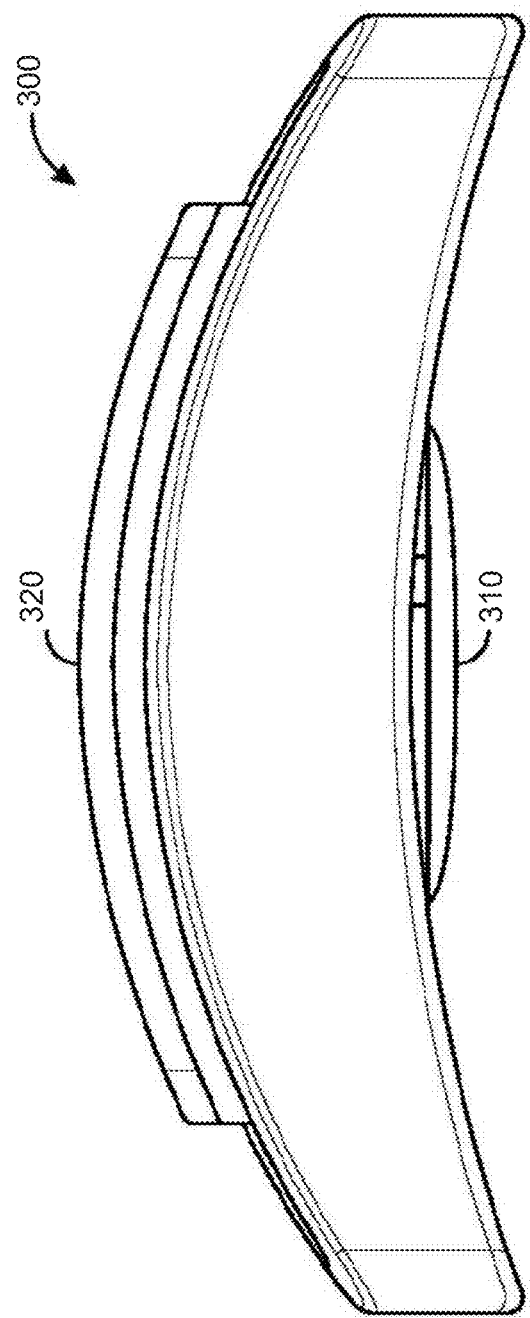
FIG. 5 illustrates a side view of the example electronic capsule.

FIG. 5 illustrates a side view of electronic capsule 300. As depicted, finger biosensor 320 may protrude from a first side of electronic capsule 300, and wrist biosensor 310 may protrude from a second side of electronic capsule 300. Casing 350 encloses components of electronic capsule 300. Casing 350 may include moldable plastic. Alternatively, casing 350 may include metal, rubber, composite material, or another, moldable material. In one embodiment, casing 350 is ultrasonically welded together to make the casing water tight and/or resistant. In alternative embodiments, other methods may be used to make the casing water tight/resistant.

Figure 6:
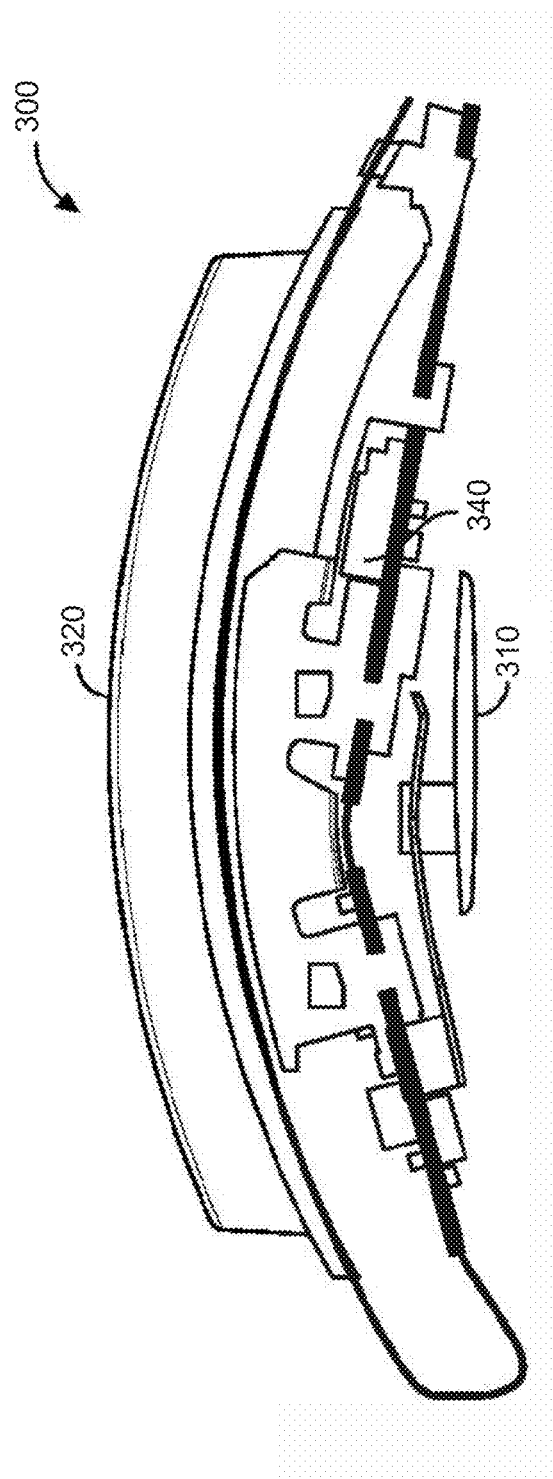
FIG. 6 illustrates a cross-sectional view of the example electronic capsule.

FIG. 6 illustrates another cross-sectional view of electronic capsule 300. In the illustrated embodiment, finger biosensor 320 protrudes from a first side of electronic capsule 300, and wrist biosensor 310 protrudes from a second side of electronic capsule 300. Both finger biosensor 320 and wrist biosensor 310 are electronically coupled to logic circuits 340.

Figure 7:
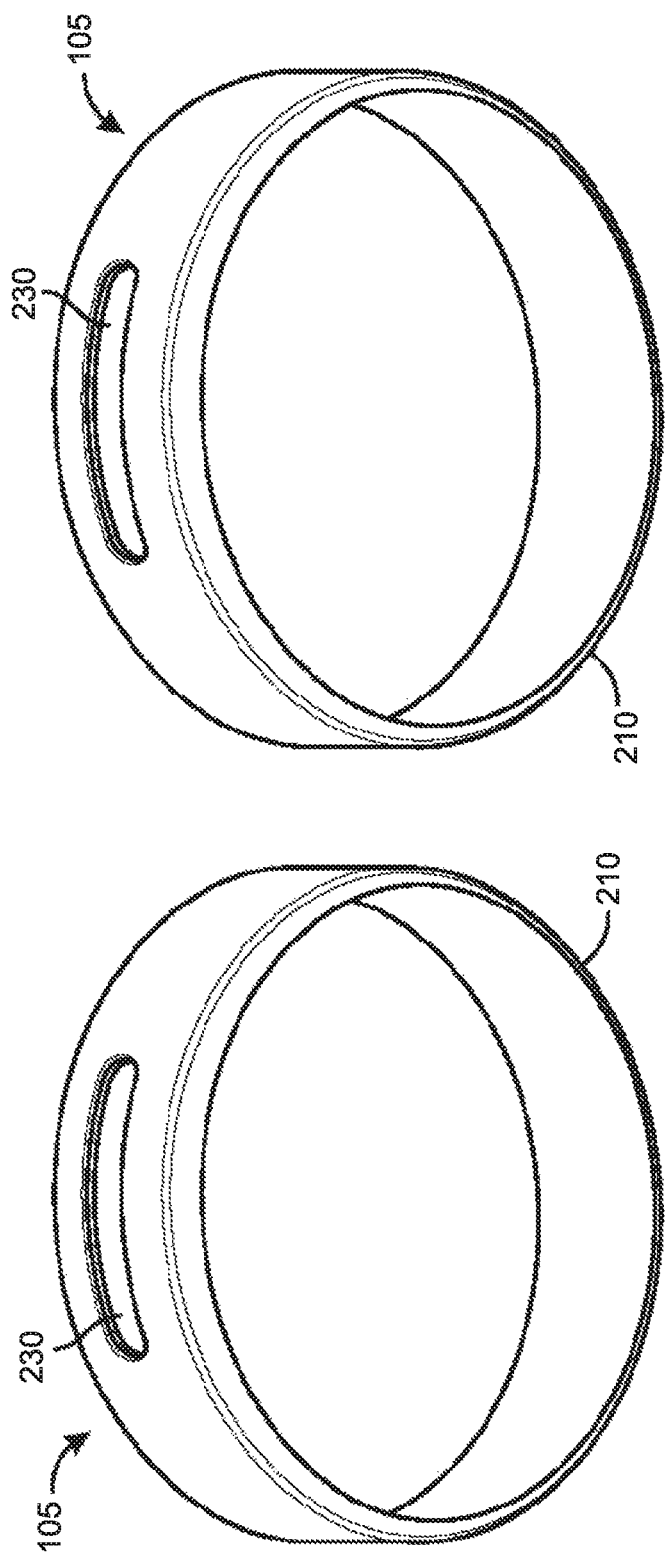
FIG. 7 illustrates a perspective view of example bands according to embodiments of the present disclosure.

FIG. 7 is a perspective view of two possible variants of band 105 that may be used in accordance with embodiments disclosed herein. Each band 105 in this embodiment includes flexible material, and aperture 230 is disposed on each band 105. Each electronic capsule 300 may be sized so as to be easily removed from one band 105 and placed in another band 105. Bands 105 may also be constructed with different dimensions, including different diameters, widths, and thicknesses, in order to accommodate different sized/shaped limbs and appendages, as well as wearer preferences. In one embodiment, bands 105 may be adjustable to accommodate different sizes/shapes of limbs. Further, bands 105 may be made in different colors, and different flexible materials, such as silicone, plastic, metal chain links, composite material, leather, synthetic leather, fabric, or other flexible materials.

In some embodiments, electronic capsule 300 may be detachably coupled to various other locations besides band 105. For example, electronic capsule 300 may be attached to a user's shoe and/or sock, coupled to sports equipment (e.g. the handle of a racket or bicycle) such that one of wrist biosensors 310 or 320 may contact parts of a user's body.

Electronic capsules 300 used in accordance with some embodiments of the presently disclosed technology may include one or more optical sensors such as a heart rate sensor or oximeter. For example, the oximeter may sense heart rate and/or HRV by detecting blood oxygenation level changes as changes in coloration at the surface of a user's skin. The optical sensor may be positioned to face radially inward towards a limb when band 105 is worn. Alternatively, the optical sensor may be separate from electronic capsule 300, but still detachably coupled to band 105 and/or electronically coupled to circuit boards that may be enclosed in electronic capsule 300 (e.g., wireless coupled or otherwise).

Referring again to FIG. 1, in various embodiments, computing device 120 may receive, process and/or display data collected, determined, and/or processed by logic circuits 340, thereby allowing the user to interact with band 105 and/or otherwise monitor the user's activity and/or biometrics, as will be further described herein. Additionally, computing device 120 may be used to collect additional activity monitoring data using sensors (e.g. biosensors, motion sensors, etc.) included in computing device 120. Further still, computing device 120 may be bi-directionally communicatively coupled (e.g., by links 125 and 130) with band 105 such that computing device 120 may be used to configure the functionality of logic circuits 340. In such cases, logic circuits 340 include a receiver as well as a transmitter.

In other embodiments, computing device 120 may connect to the Internet and receive biometric and/or activity data gathered by band 105 over a web browser. For example, the band 105 may gather/process biometric, activity, and other data, and transmit that data to a remote file server, such that computing device 120 may then access the data from the remote file server without directly linking to band 105. In yet further embodiments, computing device 120 may be mechanically coupled, electrically coupled, or both mechanically and electrically coupled to band 105, such that communication can take place over a wired or near-field connection.

Figure 8A:
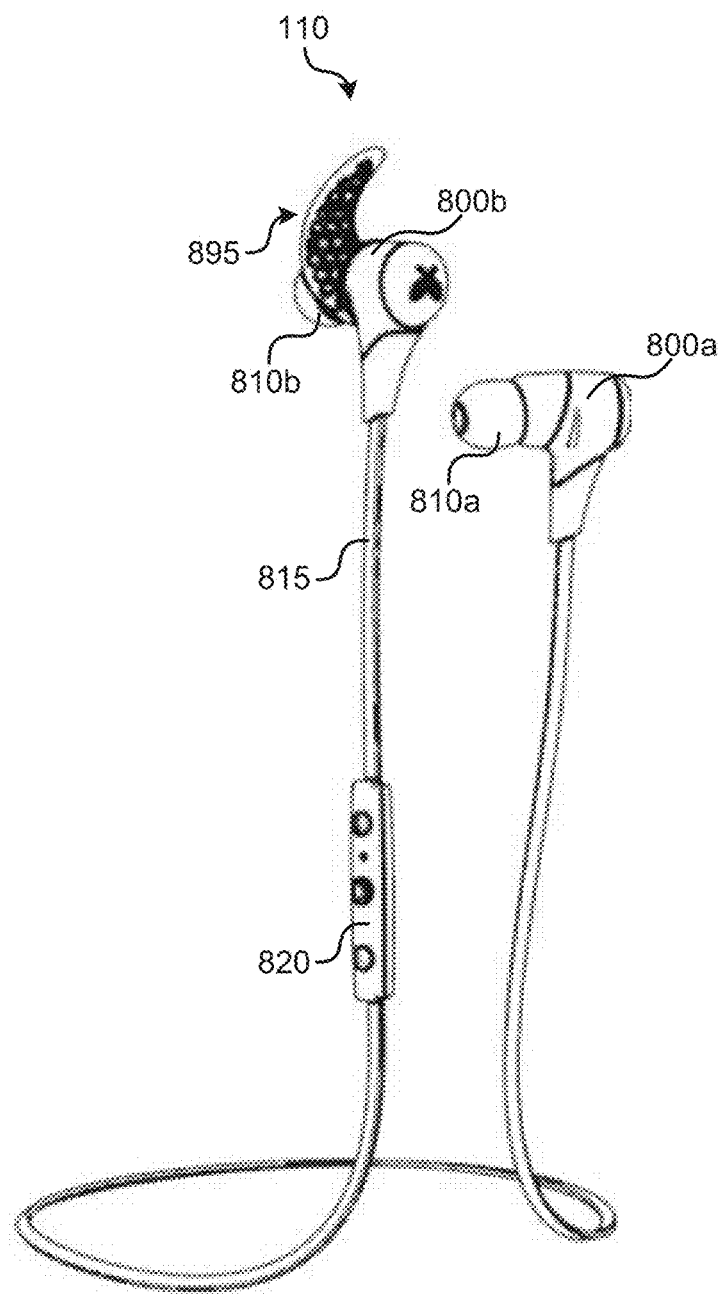
FIG. 8A illustrates a perspective view of example earphones according to embodiments of the present disclosure.

FIG. 8A illustrates a perspective view of earphones 110. FIG. 8A will generally be described in conjunction with FIG. 8B, which illustrates an example architecture of circuitry that may be used to implement earphones 110. Earphones 110 include earphone 800a, which may correspond to a wearer's right ear, and earphone 800b, which may correspond to a wearer's left ear. Generally, the aspects described herein with respect to earphone 800a may apply equally to earphone 800b, and vice versa. As shown in FIG. 8A, earphones 800a and 800b include respective tips 810a and 810b. Earphones 110 also include controller 820 and cable 815. Cable 815 electrically couples earphones 800a and 800b to one another, and also couples earphones 800a, 800b to controller 820. Additionally, earphones 800a, 800b may in some cases include fin 895 that contacts folds in the outer ear anatomy of the wearer in order to further secure the earphones 800a and/or 800b to the wearer's ear.

Earphones 110 may be constructed to have dimensions, including different diameters, widths, and thicknesses, in order to accommodate different human or animal ear sizes and different preferences. In some embodiments of earphones 110, the housing of each earphone 800a and 800b is a rigid shell that surrounds electronic components within. In some deployments, these electronic components may include components described above with respect to electronic capsule 300. In other embodiments, referring now to FIG. 8B, examples of the electronic components include motion sensor 835, optical heartrate sensor 830, audio-electronic components such as drivers 870a, 870b and speakers 805a, 805b, and other circuitry (e.g., processors 845, 850, and memories 840, 855). One or more of these components may optionally reside outside of earphones 800a, 800b, for example, in controller 820 or elsewhere. The rigid shell of the housing may be made with plastic, metal, rubber, or other materials known in the art. The housing may be cubic shaped, prism shaped, tubular shaped, cylindrical shaped, or otherwise shaped to house the electronic components or to fit well within a wearer's ear.

Referring back to FIG. 8A, tips 810a, 810b may be rounded, parabolic, and/or semi-spherical, so as to comfortably and securely fit within a wearer's ear, with the distal end of tip 810a, 810b contacting an outer rim of the wearer's outer ear canal. In some embodiments, tip 810a, 810b is removable so as to be exchanged with alternate tips of varying dimensions, colors, or designs to accommodate a wearer's preference and/or fit more closely match the radial profile of the wearer's outer ear canal. Tip 810a, 810b may be made with softer materials such as rubber, silicone, fabric, or other materials as would be appreciated by one of ordinary skill in the art upon studying the present disclosure.

Controller 820 may provide various controls (e.g., buttons and switches) related to media playback, such as, for example, volume adjustment, track skipping, audio track pausing, and the like. Additionally, controller 820 may include various controls related to the gathering of biometrics and/or activity information, such as, for example, controls for enabling or disabling heart rate and motion detection. Controller 820 may be of a simple design having, for example, three buttons to perform various of the controls described herein.

Figure 8B:
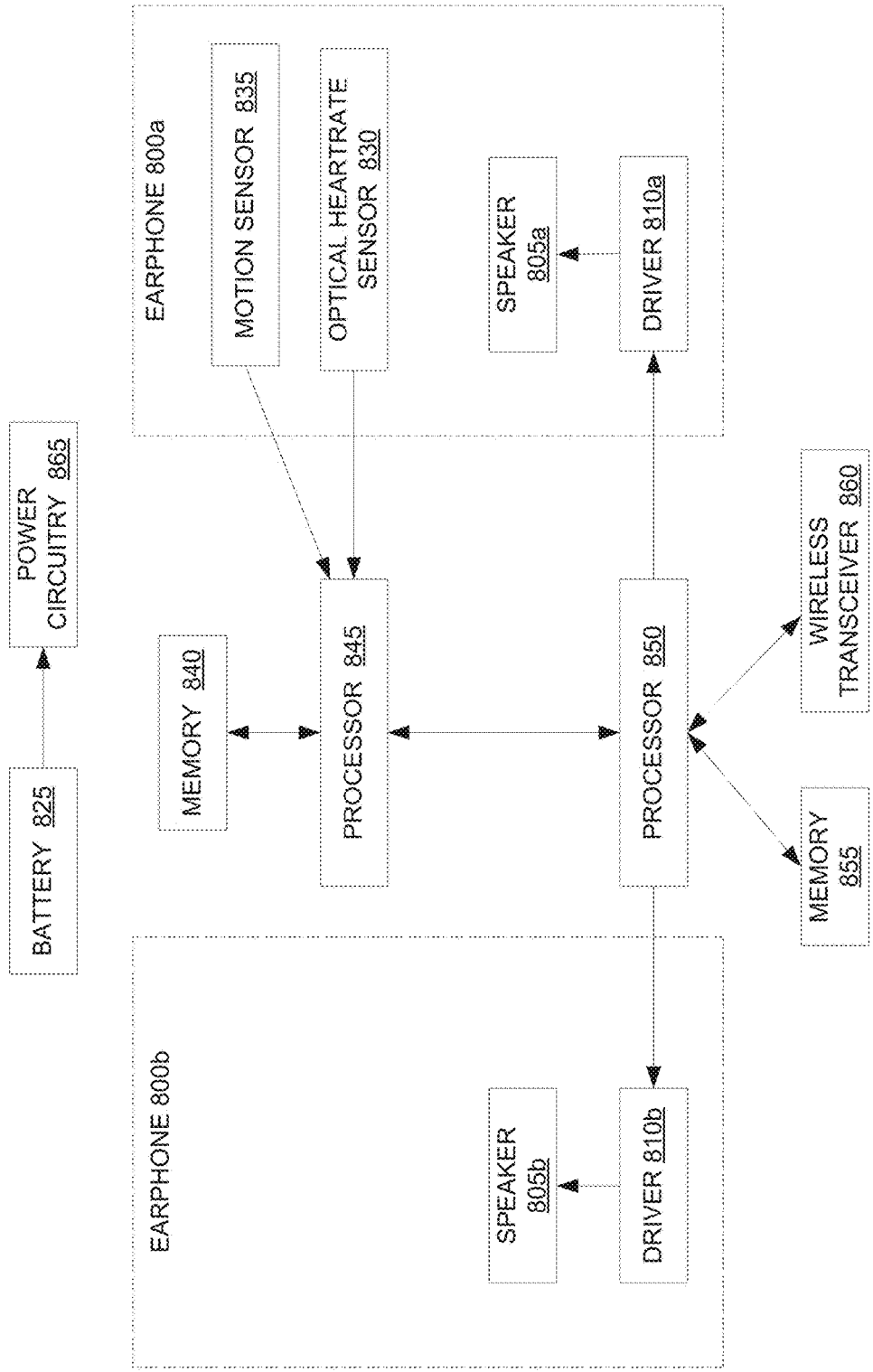
FIG. 8B illustrates an example architecture for circuitry of earphones according to embodiments of the present disclosure.

With reference to FIG. 8B, the circuitry of earphones 110 may include processors 845, 850 (including, in some instances, logic circuits similar to logic circuits 340), memories 840, 855, wireless transceiver 860, battery 825, power circuitry 865, and other circuitry for earphones 800a, 800b. As further illustrated earphone 800a may include motion sensor 835, optical heartrate sensor 830, speaker 805a, and driver 870a. Earphone 800b may include any of these components, and in the illustrated embodiment includes speaker 805b and driver 870b. In additional embodiments, earphone 800b may also include a motion sensor (e.g., an accelerometer or gyroscope, generally, similar to motion sensor 835), and/or an optical heartrate sensor (e.g., optical heartrate sensor 830). Motion sensor 835, including any subcomponents thereof (e.g., as described above), and/or optical heartrate sensor 830 may be included entirely within a single earphone (e.g., earphone 800a), may be distributed between two earphones 800a, 800b, or may be duplicated within each earphone 800a, 800b in any combination for added precision, such that each earphone 800a, 800b in the pair can detect and activity and biometrics information as desired for particular applications.

Processor 845 may include logic circuits for receiving, processing, and/or storing information gathered by biosensors (e.g., optical heartrate sensor 830) and/or motion sensor 835. More particularly, as illustrated in FIG. 8B, processor 845 may be coupled (e.g., by wired or wireless connection) to motion sensor 835 and optical heartrate sensor 830, and hence may receive and process electrical signals generated by these sensors 835 and/or 830 in response to the wearer's motion and biometrics, respectively. Processor 845 may store such signals or processed versions thereof as biometric data and/or activity data in memory 840, which biometric data and/or activity data may be made available to a computing device 120 using wireless transceiver 860. In some embodiments, memory 840 stores biometric data and/or activity data for transmission by wireless transceiver 860 to computing device 120 for further processing thereby.

During operation, optical heartrate sensor 830 may use a photoplethysmogram (PPG) to optically obtain the user's heart rate. In one embodiment, optical heartrate sensor 830 includes a pulse oximeter that detects blood oxygenation level changes as changes in coloration at the surface of a user's skin. More particularly, in this embodiment, optical heartrate sensor 830 illuminates the skin of the user's ear using a light-emitting diode (LED). Light from the LED penetrates through the epidermal layers of the skin to underlying blood vessels. A portion of the light is absorbed, while a portion of the light is reflected back to optical heartrate sensor 830. The light reflected back through the skin of the user's ear is then obtained with a receiver (e.g., a photodiode) and used to detect changes in the user's blood oxygen saturation ($SpO_2$) and pulse rate, thereby permitting calculation of the user's heart rate using algorithms known in the art (e.g., using processor 845). Optical heartrate sensor 830 may be positioned on one of earphones 800a, 800b such that optical heartrate sensor 830 is proximal to the interior side of a user's tragus when earphones 110 are worn. In other embodiments, optical heartrate sensor 830 may be positioned on one of earphones 800a, 800b so as to be proximal to any other portion of the user's ear (e.g. concha, ear lobe, pinna, antitragus, outer ear canal, etc.) when earphone 800a, 800b is worn by the user.

In this manner, optical heartrate sensor 830 may also be used to generate biometrics that may be used calculate or estimate the wearer's heart rate variability (HRV), i.e. the variation in time interval between consecutive heartbeats. For example, processor 845 or a processor resident in computing device 120 may calculate HRV using the biometrics gathered by optical heartrate sensor 830 based on a time domain methods, frequency domain methods, and/or other methods known in the art that estimate/calculate HRV based on data such as mean heart rate, change in pulse rate over a time interval, and other data used in the art to estimate/calculate HRV. These methods of calculating HRV may also be applied with respect to biometrics gathered using band 105.

In further embodiments, logic circuits of processor 845 may further detect, calculate, and/or store activity data, based on measured activity of the wearer, such as the wearer's amount of physical activity (e.g., exercise and the like), sleep, or rest over a period of time, or the amount of time without physical activity over a period of time. The logic circuits may use the HRV, the activity data, or some combination of the two to gauge the wearer's response to the activity and other external factors (e.g., temperature, weather, stress, etc.). In various embodiments, the user's response may indicate the user's physical condition and aptitude for further physical activity for the current or next day, as will be described in further detail herein.

Referring again to FIG. 8B, during audio playback, earphones 110 may wirelessly receive audio data using wireless transceiver 860. The audio data may then be processed by logic circuits of processor 850, for example to be converted into electrical signals and delivered to respective drivers 870a, 870b of speakers 805a, 805b, such that the electrical signals may be converted to sound. Drivers 870a, 870b may use various driver technologies known in the art, for example, moving coil drivers, electrostatic drivers, electret drivers, orthodynamic drivers, and other transducer technologies may be used.

Wireless transceiver 860 may be configured to transmit/receive biometrics, activity, and audio data across link 125 and 130, for example using available wireless communications protocols/standards or methods. In some embodiments, wireless transceiver 860 may utilize BLUETOOTH, ZIGBEE, Wi-Fi, GPS, cellular technology, or some combination thereof. Further, although FIG. 8B illustrates a single wireless transceiver 860 for transmitting/receiving biometrics, activity, and audio data, in an alternative embodiment, separate transceivers may be dedicated for communicating biometric data to/from computing device 120, for communicating activity data to/from computing device 120, and for communicating audio data to/from computing device 120. In some cases, transceiver 860 may include a low energy transmitter such as a near field communications (NFC) transmitter or a BLUETOOTH low energy (LE) transmitter. In further example implementations, a separate wireless receiver may be provided for receiving high fidelity audio data from an audio source. In yet additional embodiments, a wired interface (e.g., micro-USB) may be used for communicating data stored in memories 840 and/or 855.

FIG. 8B also shows that earphones 110 may be powered by battery 825, which may be coupled to power circuitry 865. Any suitable battery or power supply technologies known in the art may be used. For example, a lithium-ion battery, aluminum-ion battery, piezo or vibration energy harvesters, photovoltaic cells, or other like devices may be used. In some deployments of earphones 110, battery 825 may be enclosed in earphone 800a or 800b. Alternatively, battery 825 may be enclosed in controller 820. The circuitry of earphones 110 described herein may be configured to enter a low-power or inactive mode when earphones 110 are not in use, or in other scenarios where low-power operation is appropriate. For example, mechanisms such as an on/off switch, a BLUETOOTH transmission disabling command, or the like may be provided by controller 820, such that a user may manually control the on/off state of one or more power-consuming components or circuits of earphones 110.

It should be noted that in various embodiments, processors 845 and 850, memories 840 and 855, wireless transceiver 860, battery 825, and power circuitry 865 may be enclosed in and/or distributed throughout either or both of earphone 800a, earphone 800b, and controller 820. For example, processor 845 and memory 840 may be enclosed in earphone 800a along with optical heartrate sensor 830 and motion sensor 835. In this particular scenario, these components may be electrically coupled to a printed circuit board (PCB) enclosed in earphone 800a. Additionally, any one or more of these components may be duplicated in each of earphones 800a, 800b. It should also be noted that although processors 845 and 850 are illustrated as being separate from one another, the functions of processors 845 and 850 may be integrated into a single processor.

Figure 9C:
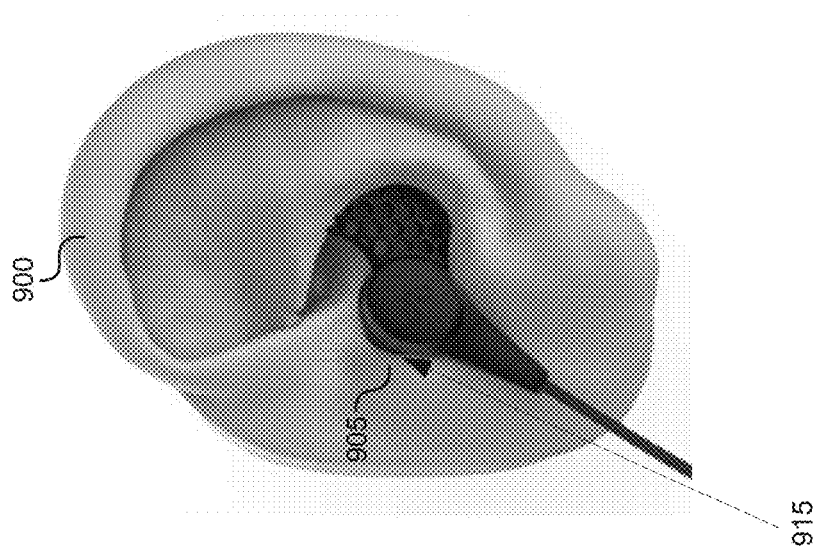
FIG. 9C illustrates a frontal perspective view of embodiments of an example earphone placed in a user's ear in accordance with the present disclosure.
Figure 9B:
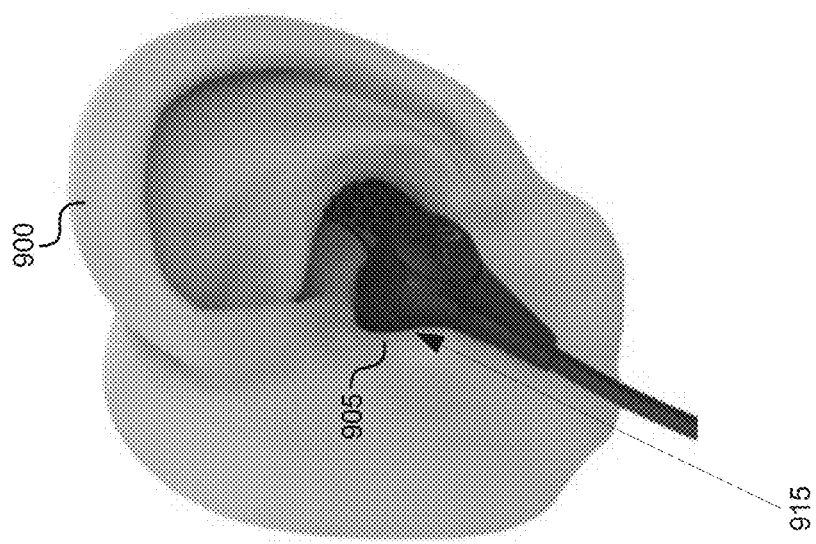
FIG. 9B illustrates a side view of embodiments of an example earphone placed in a user's ear in accordance with the present disclosure.
Figure 9A:
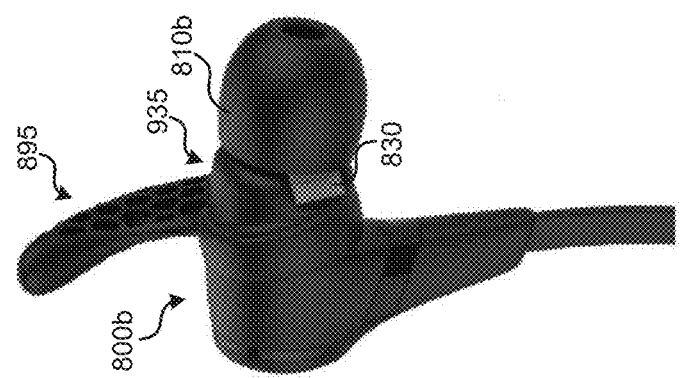
FIG. 9A illustrates a perspective view of embodiments of an example earphone in accordance with the present disclosure.

FIG. 9A illustrates a perspective view of embodiments of earphone 800b. As shown, earphone 800b may include optical heartrate sensor 830, as generally described above. FIG. 9A will be described in conjunction with FIGS. 9B and 9C, which show various perspective views illustrating example arrangements of optical heartrate sensor 830 when earphone 800b (or 800a) is worn in a user's ear 900. As shown, earphone 800b may include body 935, tip 810b, fin 895, and optical heartrate sensor 830. Optical heartrate sensor 830 protrudes from a frontal side of body 935, proximal to tip 810b, and proximal to a nozzle (not shown) of earphone 800b. FIGS. 9B and 9C illustrate interface 915 of optical heartrate sensor 830 and ear 900 when earphone 800b is worn in a user's ear 900. In the illustrated embodiments, when earphone 800b is worn, optical heartrate sensor 830 is proximal to the interior side of the user's tragus 905. In various embodiments, earphones 800a, 800b may be dual-fit earphones shaped to be comfortably and securely worn in either an over-the-ear configuration or an under-the-ear configuration. The secure fit provided in such embodiments aids in keeping optical heartrate sensor 830 positioning on the interior side of tragus 905, thereby ensuring accurate and consistent measurements of a user's heartrate information.

Figure 9F:
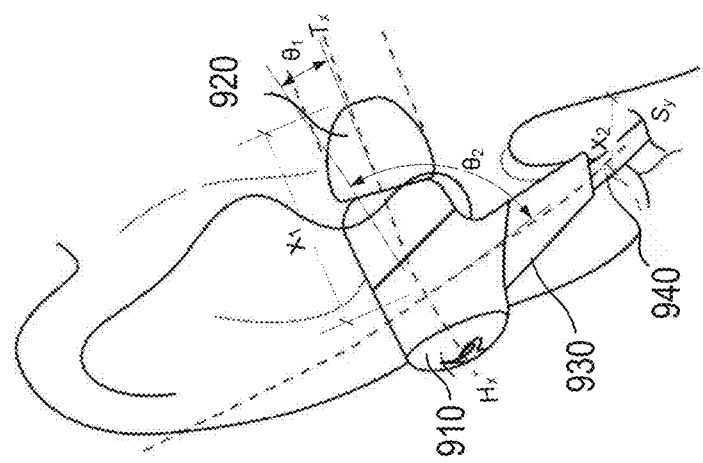
FIG. 9F illustrates a cross-sectional view of an example earphone according to embodiments of the present disclosure.
Figure 9E:
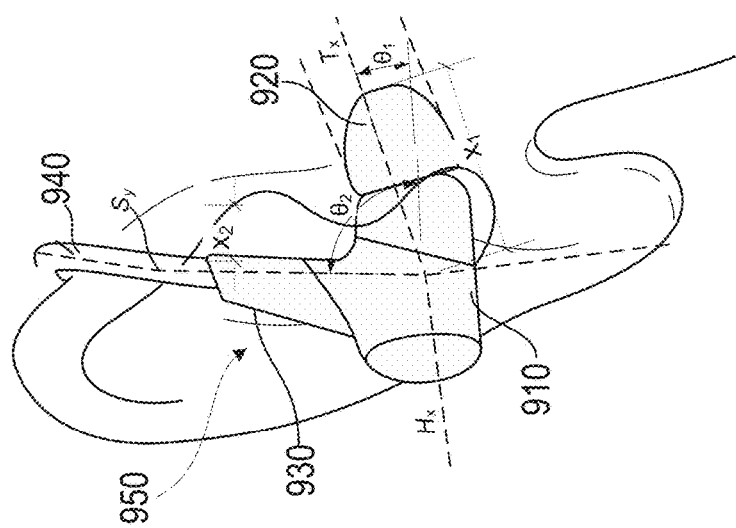
FIG. 9E illustrates a cross-sectional view of an example earphone according to embodiments of the present disclosure.
Figure 9D:
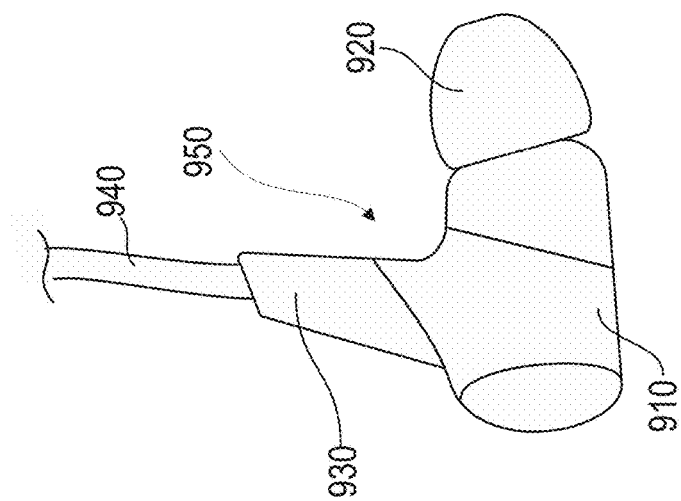
FIG. 9D illustrates a cross-sectional view of an example earphone according to embodiments of the present disclosure.

FIGS. 9D and 9E illustrate earphones 950 in an over-the-ear configuration, whereas FIG. 9F illustrates earphones 950 in an under-the-ear configuration. As illustrated, earphone 950 includes housing 910, tip 920, strain relief 930, and cable 940. The proximal end of tip 920 mechanically couples to the distal end of housing 910. Similarly, the distal end of strain relief 930 mechanically couples to a side (e.g., the top side) of housing 910. Furthermore, the distal end of cable 940 may be disposed within and secured by the proximal end of strain relief 930.

Referring to FIGS. 9E and 9F, the longitudinal axis of housing 910, $H_x$, forms angle $\theta_1$ with respect to the longitudinal axis of tip 920, $T_x$. The longitudinal axis of strain relief 930, $S_y$, may align with the proximal end of strain relief 930 and form angle $\theta_2$ with respect to the axis $H_x$. In some embodiments, $\theta_1$ is greater than 0 degrees, e.g., $T_x$ extends in at an angle from $H_x$, or in other words, tip 920 may be angled with respect to housing 910. The value of $\theta_1$ may be selected to approximate the ear canal angle of the wearer. For example, $\theta_1$ may range between 5 degrees and 15 degrees, and may extend from 0 degrees 45 degrees. Also, $\theta_2$ may be less than 90 degrees, e.g., such that $S_y$ extends at a non-orthogonal angle from $H_x$, or in other words, strain relief 930 is angled with respect to a perpendicular orientation with housing 910. In some embodiments, $\theta_2$ may be selected to direct the distal end of cable 940 closer to the wearer's ear. For example, $\theta_2$ may range between 75 degrees and 89 degrees, but may extend to as low as 45 degrees in some situations.

As further illustrated in FIGS. 9E and 9F, $x_1$ may represent the distance between the distal end of tip 920, on the one hand, and the intersection of strain relief 930's longitudinal axis $S_y$ and housing longitudinal axis $H_x$, on the other hand. One of skill in the art would, upon studying the present disclosure, appreciate that the dimension $x_1$ may be selected based on several parameters, including, for example, the desired fit to a wearer's ear based on the average human ear anatomical dimensions, the types and dimensions of electronic components (e.g., optical heartrate sensor 830, motion sensor 835, processors 845 and 850, memories 840 and 855, other components described in this connection, and so on) that may be disposed within housing 910 and tip 920, and based on the specific placement of optical heartrate sensor 830. In some examples, $x_1$ may be at least 18 mm. However, in other examples, $x_1$ may be smaller or greater based on the parameters discussed above.

Referring again to FIGS. 9E and 9F, $x_2$ may represent the distance between the proximal end of strain relief 930 and the surface of the wearer's ear. In the illustrated configurations, $\theta_2$ may be selected to reduce $x_2$, as well as to direct cable 940 toward the wearer's ear, such that cable 940 may rest in the crevice formed where the top of the wearer's ear meets the side of the wearer's head. In some embodiments, $\theta_2$ may range between 75 degrees and 89 degrees, but may extend to as low as 45 degrees in some situations.

In some examples, strain relief 930 may be made of a flexible material such as rubber, silicone, or soft plastic, so as to enable strain relief 930 to be bent toward the wearer's ear. Similarly, strain relief 930 may include a shape memory material so as to retain the shape thereof after being bent inward. In some examples, strain relief 930 may be shaped to curve inward towards the wearer's ear.

As one having skill in the art would appreciate from the above description, earphones 110 and band 105 may in various embodiments gather biometric data and activity data that may be used to track a user's activities and activity level. The biometric data and activity data may then be made available to computing device 120, which may provide a GUI for interacting with the data using a tracking application installed on computing device 120. FIG. 10A is a block diagram illustrating example components of computing device 120, including an installed tracking application (occasionally referred to as an app) 1015.

With continued reference to FIG. 10A, computing device 120 may include connectivity interface 1005, storage 1010 that stores tracking application 1015, processor 1020, graphical user interface (GUI) 1025 that may be provided on display 1030, and bus 1035 for transferring data between the various components of computing device 120. Connectivity interface 1005 connects computing device 120 to earphones 110 and/or band 105 through a communication medium (e.g., links 125 and 130). Storage 1010 may include volatile memory (e.g. RAM), non-volatile memory (e.g. flash storage), or some combination/variation thereof. In various embodiments, storage 1010 may store biometric data and/or activity data collected by earphones 110 and/or band 105. Additionally, storage 1010 may store tracking application 1015 that, when executed by processor 1020, receives input (e.g., by a conventional hard/soft key or a touch screen, voice detection, or other input mechanism), and allows a user to interact with the collected biometric and/or activity data.

In various embodiments, a user may interact with tracking application 1015 via GUI 1025, which may be provided by display 1030, for example, a touchscreen display that accepts various hand gestures as inputs. Tracking application 1015 may process the biometric and/or activity data collected by earphones 110 and/or band 105, and present the data via display 1030. Before describing tracking application 1015 in further detail, it should be noted that in some embodiments earphones 110 and band 105 may filter the collected biometric and activity data prior to transmitting the same to computing device 120. Accordingly, although the embodiments disclosed herein are described with reference to tracking application 1015 processing the received data, in various implementations, preprocessing operations, and/or any one or more of the other processing operations disclosed herein, may be performed by processors 845 or 850 of earphones 110, or by logic circuits 340, prior to transmission of the data to computing device 120.

Tracking application 1015 may be initially configured/setup (e.g., after installation on a smartphone or other computing device 120) based on a user's self-reported biological information, sleep information, and activity preference information. For example, during setup, the user may be prompted via display 1030 to enter biological information such as the user's gender, height, age, weight, etc. Further, during setup the user may be prompted for sleep information, such as the amount of sleep needed by the user and the user's regular bed/wake time. Further still, the user may be prompted during setup for a preferred activity level and/or intensity, as well as types of activities the user desires to be tracked (e.g., running, walking, swimming, dancing, biking, hiking, etc.) In various embodiments of the disclosure, this self-reported information may be used in tandem with the information collected by earphones 110 and/or band 105.

Following the setup, tracking application 1015 may be used by a user to monitor activity and biometrics of the user (e.g., based on sensors 835 and 830). As further illustrated in FIG. 10B, tracking application 1015 may include various modules, such as, for example display module 1050, biosensor module 1055, performance profile module 1060, and motion sensor module 1065. These modules may be implemented separately or in combination. Each module may include computer-readable media and have computer-executable code stored thereon, such that the code may be executed by processor 1020 (e.g., in some cases in conjunction with processing modules 1070) to perform specific functions (e.g., as described herein with regard to various flow charts etc.) with respect to biometric and/or activity data available to tracking application 1015. As will be further described below, display module 1050 may present (e.g., via display 1030) various screens to a user, with the screens containing graphical representations of information provided by tracking application 1015. In further embodiments, tracking application 1015 may be used to display to the user an instruction for wearing and/or adjusting earphones 110.

FIG. 11 is an operational flow diagram illustrating example method 1100 that provides an earphone adjustment feedback loop to increase the likelihood of accurate biometric data collection by earphones 110. At operation 1110, tracking application 1015 may be executed, which may in turn result in displaying an instruction to the user on how to wear earphones 110 to obtain an accurate and reliable signal from optical heartrate sensor 830 and/or motion sensor 835. Operation 1110 may occur only once, upon installation of tracking application 1015, may occur once per day (e.g., when the user first wears earphones 110 in the day), or at any customizable, programmable, and/or predetermined interval.

Operation 1120 involves providing feedback (e.g., by a display such as display 1030 on computing device 120) to the user regarding the quality of the signal received from one or both of optical heartrate sensor 830 and/or motion sensor 835, based on the positioning of earphones 110. For example, a signal quality bar or other graphical elements may be displayed to the user. Alternatively, an audio signal may be used to provide the feedback.

At decision 1130, it is determined if the biosensor signal quality is satisfactory for accurate biometric and activity data to be gathered/used. In various embodiments, this determination may be based on factors such as, for example, the frequency with which optical heartrate sensor 830 is collecting heart rate data and/or with which motion sensor 835 is collecting activity information, the variance in the measurements of optical heartrate sensor 830 and/or activity information (including location-based information), dropouts in heart rate measurements by sensor 830, the signal-to-noise ratio approximation of optical heartrate sensor 830 and/or motion sensor 835, the amplitude of the signals generated by sensors 835 and/or 830, and the like.

If the signal quality is determined (e.g., at decision 1130) to be unsatisfactory, at operation 1040, tracking application 1015 may display instructions for adjusting earphones 110 to improve the signal, and operations 1120 and decision 1130 may subsequently be repeated. For example, instruction on adjusting strain relief 930 of earphone 950 may be displayed. Otherwise, if the signal quality is satisfactory, at operation 1150, tracking application 1015 may display confirmation of good signal quality and/or good position of earphones 110. Subsequently, tracking application 1015 may proceed with normal operation.

Figure 12A:
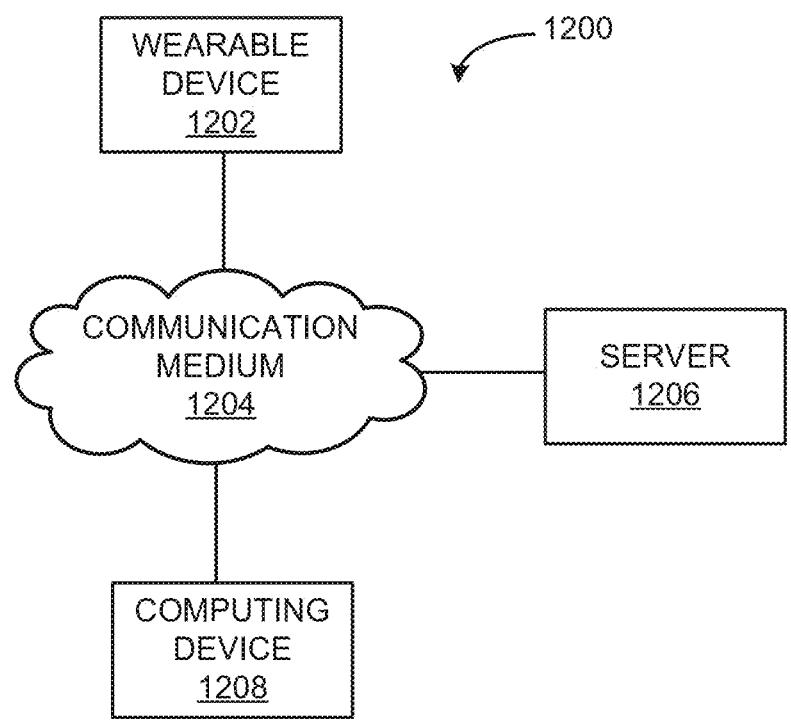
FIG. 12A is an example system in which various embodiments of the disclosure may be implemented.

FIG. 12A illustrates example system 1200 in which various embodiments of the disclosure may be implemented. By way of example, system 1200 may be used to determine performance capacity of a user. System 1200 includes wearable device 1202, communication medium 1204, server 1206, and computing device 1208. Embodiments of system 1200 are capable of capturing and tracking robust information related to a user's activity, including information about the user's activity type, duration, intensity, and so on. Moreover, embodiments of system 1200 are also capable of tracking and capturing and tracking robust information related to a user's biometrics. This wealth of information, which may be gathered by various sensors as described herein, may be used to provide a user-specific response profile that is based on biometric and/or activity data. Being user-specific, the response profile provided by system 1200 may be personalized and accurate. Further, in some embodiments, a model may be created based on the gathered activity/biometric data, such that the response profile may be used to predict the user's response to various training loads.

An accurate and personalized response profile of the above-described nature may allow the user to make informed decisions regarding the user's training load and/or lifestyle, thus achieving maximum performance and balance. For example, the response profile may generally indicate how a user is likely to respond to a given training load or other activity or set of conditions. This indication, in some embodiments, represents the user's performance capacity (e.g., the user's capacity to undertake a given training load, perform a given activity, etc.). Such an indication may be provided to a user in one or more of an audio, visual, numerical, descriptive, or graphical representation (e.g., via display 1030 of computing device 120, etc.). For instance, if the indication is provided on a scale from 0 to 100, and the response profile indicates a 75 on this scale, this indication may be provided to a user in a bar graph, a scale, a numeral, a digital gauge, a textual description, or the like (e.g., a bar graph depicted as being filled ¾ of the way). In some such embodiments, a 0 on the response profile scale may represent little to no capacity to perform the activity (e.g., the user's biometrics reflect that the user has been working or active for 24 hours straight with no sleep, and the user thus needs rest immediately), and a 100 on the response profile scale may represent full capacity (e.g., the user's biometrics reflect that the user is well-rested and otherwise ready for activity). Of course, any scale may be implemented without departing from the scope of the present disclosure, as indicated previously. Thus, the response profile created and provided by the systems, methods, and devices of the present disclosure may enable a user to intelligently assess the user's capacity for activity, whether to be undertaken immediately or sometime in the future.

Referring again to FIG. 12A, wearable device 1202 may include in some embodiments, band 105 or earphones 110. Communication medium 1204 may be used to connect or communicatively couple wearable device 1202, server 1206, and/or computing device 1208 to one another or to a network, and communication medium 1204 may be implemented in a variety of forms. For example, communication medium 1204 may include an Internet connection, such as a local area network (LAN), a wide area network (WAN), a fiber optic network, internet over power lines, a hard-wired connection (e.g., a bus), and the like, or any other kind of network connection. Communication medium 1204 may be implemented using any combination of routers, cables, modems, switches, fiber optics, wires, radio (e.g., microwave/RF links), and the like. Further, communication medium 1204 may be implemented using various wireless standards, such as Bluetooth®, Wi-Fi, 3GPP standards (e.g., 2G GSM/GPRS/EDGE, 3G UMTS, or 4G LTE), etc. Upon reading the present disclosure, one of skill in the art will recognize other ways to implement communication medium 1204 for communications purposes.

Server 1206 generally directs communications made over communication medium 1204. Server 1206 may include, for example, an Internet server, a router, a desktop or laptop computer, a smartphone, a tablet, a processor, a module, or the like, and may be implemented in various forms, include, for example, an integrated circuit, a printed circuit board, or in a discrete housing/package. In one embodiment, server 1206 directs communications between communication medium 1204 and computing device 1208. For example, server 1206 may update information stored on computing device 1208, or server 1206 may send/receive information to/from computing device 1208 in real time. Server 1206 may also be used to implement cloud computing capabilities for wearable device 1202 and/or computing device 1208.

Computing device 1208 may take a variety of forms, such as a desktop or laptop computer, a smartphone, a tablet, a smartwatch or other wearable electronic device, a processor, a module, earphones, or the like. By way of illustration, computing device 1208 may include a processor or module embedded in a wearable sensor, a bracelet, a smart-watch, a piece of clothing, an accessory, and so on. Computing device 1208 may be, for example, substantially similar to devices embedded in electronic capsule 200, which may be embedded in and/or removable from band 105, as illustrated in FIGS. 2 through 7 and described herein. Computing device 1208 may communicate with other devices over communication medium 1204 with or without the use of server 1206. In one embodiment, wearable device 1202 includes computing device 1208. Further, computing device 1208 may in some cases be computing device 120 or be substantially similar thereto, and in this regard, the description of computing device 120 herein may apply equally to computing device 1208, and vice versa. In various embodiments, wearable device 1202 or computing device 1208 may be used to perform various processes described herein and/or may be used to execute various operations described herein with regard to one or more disclosed systems and methods. Upon studying the present disclosure, one of skill in the art will appreciate that system 1200 may include multiple wearable devices 1202, communication media 1204, servers 1206, and/or computing devices 1208.

Figure 12B:
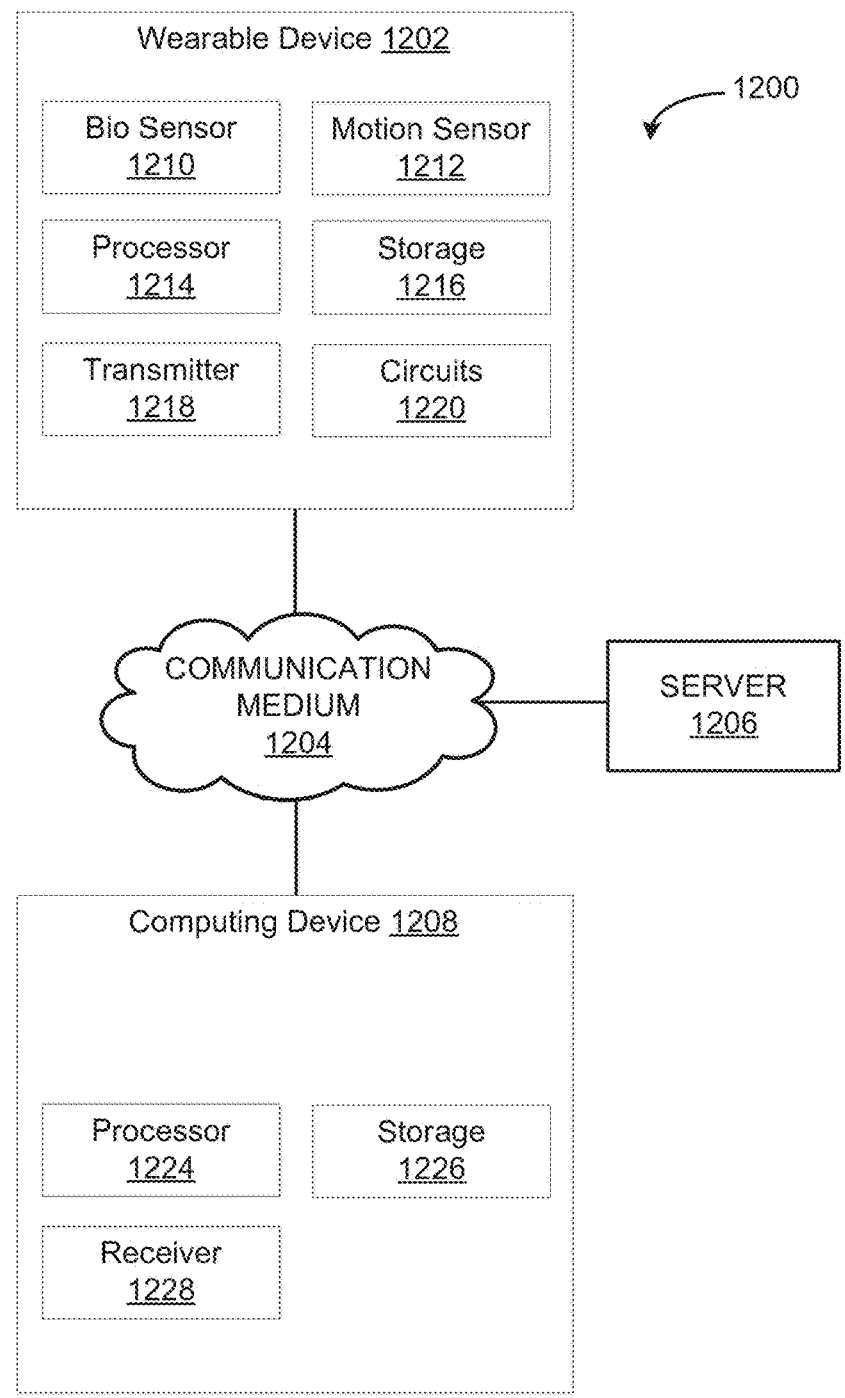
FIG. 12B is an example system in which various embodiments of the disclosure may be implemented.

FIG. 12B illustrates one embodiment of system 1200, and specifically, provides further detail of some example implementations of wearable device 1202 and computing device 1208, in accordance with the present disclosure. In the embodiments of FIG. 12B, wearable device 1202 includes biosensor 1210 and motion sensor 1212. In one specific example, wearable device 1202 further includes processor 1214. Processor 1214 may be coupled to biosensor 1210 and motion sensor 1212, and may be configured to process electrical signals generated by biosensor 1210 and/or motion sensor 1212. Such signals may be indicative of biometrics and activity, as will is described in further detail herein. Biosensor 1210 may be implemented as any of the various sensors described herein for measuring biometrics of a user—e.g., with respect to FIGS. 1 through 11. In this connection, biosensor 1210 may include one or more sensors, e.g., finger biosensor 320, wrist biosensor 310, and optical heartrate sensor 830. Likewise, motion sensor 1212 may be implemented as any of the various motion sensors described herein for detecting motion (e.g., by way of various inertial units), as described, e.g., with reference to FIGS. 1 through 11.

Furthermore, wearable device 1202 may include circuits 1220 that receive and process the electrical signals from biosensor 1210 and motion sensor 1212. For example, circuits 1220 may include an analog-to-digital converter, an encoder, modem circuitry, and the like, that receive electrical signals from biosensor 1210 and motion sensor 1212 and process the electrical signals into a format that may be acceptable to processor 1214 or that may be transmitted over communication medium 1204 by transmitter 1218. Storage 1216 may also be included in embodiments of wearable device 1202, and may be used to store activity data and/or biometric data generated from the electrical signals output by biosensor 1210 and/or motion sensor 1212. This stored data may then be processed by processor 1214 and used locally to wearable device 1202, or be transmitted by transmitter 1218. Additionally, storage 1216 and 1226 may include non-transitory computer-readable media having instructions stored thereon that, when executed, cause processor 1214 and/or 1224 to perform various functions, including, by way of example, any of the operations described with reference to methods 1300 (and FIGS. 13A, 13B, and 13C) and elsewhere herein, and to make various calculations, or control or communicate with any of the other various other hardware components described herein.

As further depicted in FIG. 12B, system 1200 for determining performance capacity also includes receiver 1228. Receiver 1228 may be part of and/or embedded within computing device 1208 (e.g., may be implement at least in part as an integrated circuit). Receiver 1228 may be a wireless receiver, and receiver 1228 receives biometric data and activity data. For example, receiver 1228 may receive the biometric and activity data over communications medium 1204 from transmitter 1218. The biometric data may be indicative of biometrics measured by biosensor 1210 in wearable device 1202, and the activity data may be indicative of activity data monitored by motion sensor 1212.

Figure 13A:
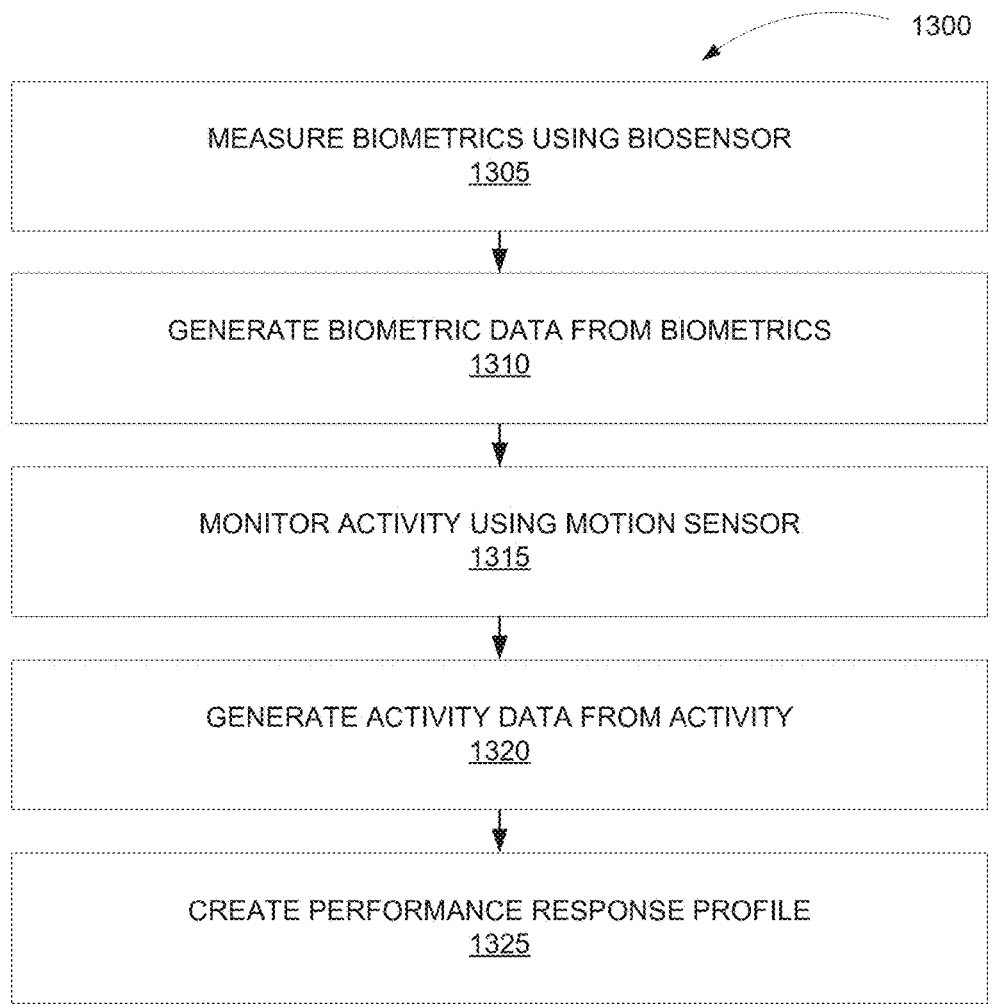
FIG. 13A is an example operational flow diagram illustrating various operations that may be performed to determine performance capacity in accordance with various embodiments described herein.
Figure 13B:
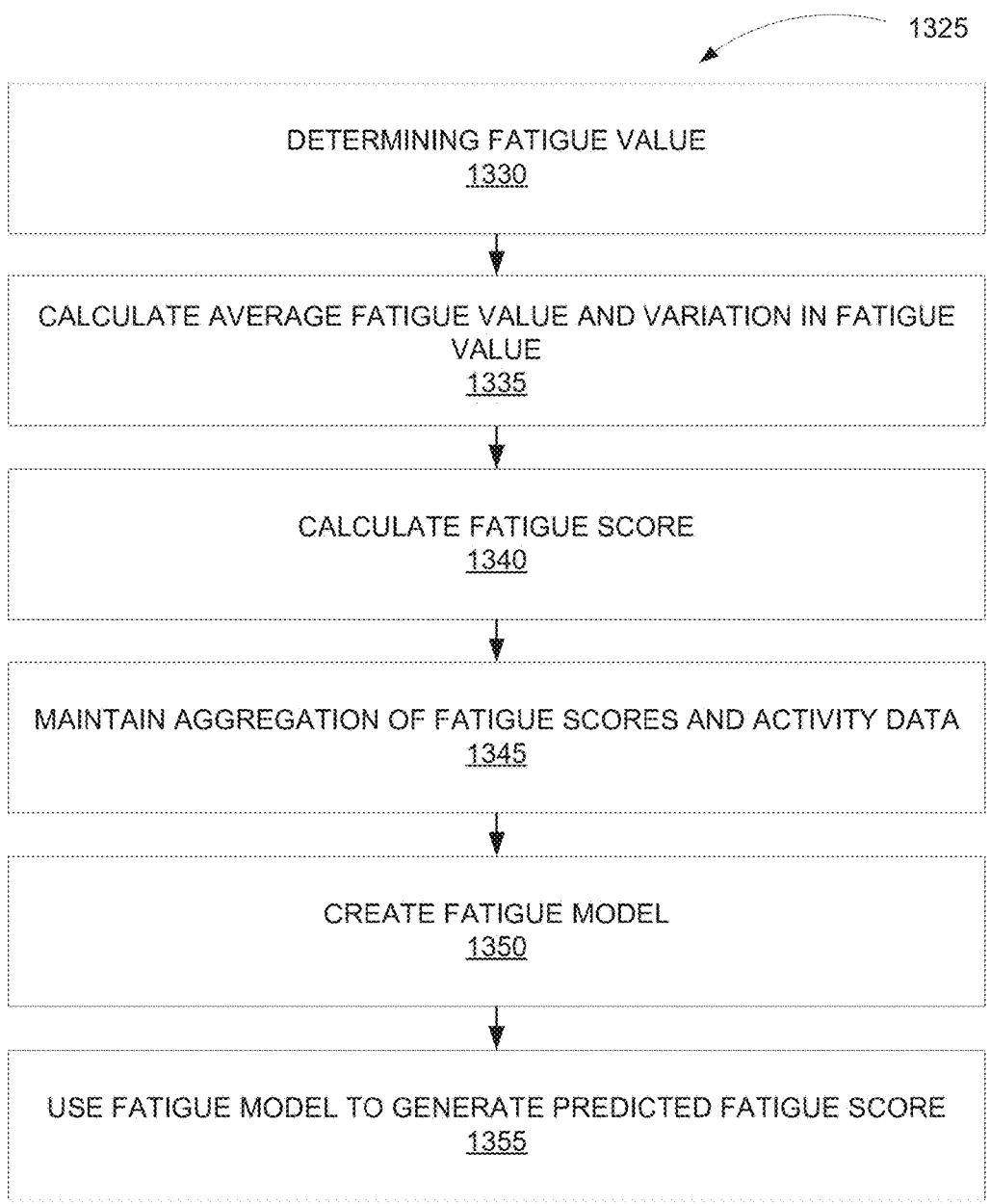
FIG. 13B is an example operational flow diagram illustrating various operations that may be performed to determine performance capacity in accordance with various embodiments described herein.
Figure 13C:
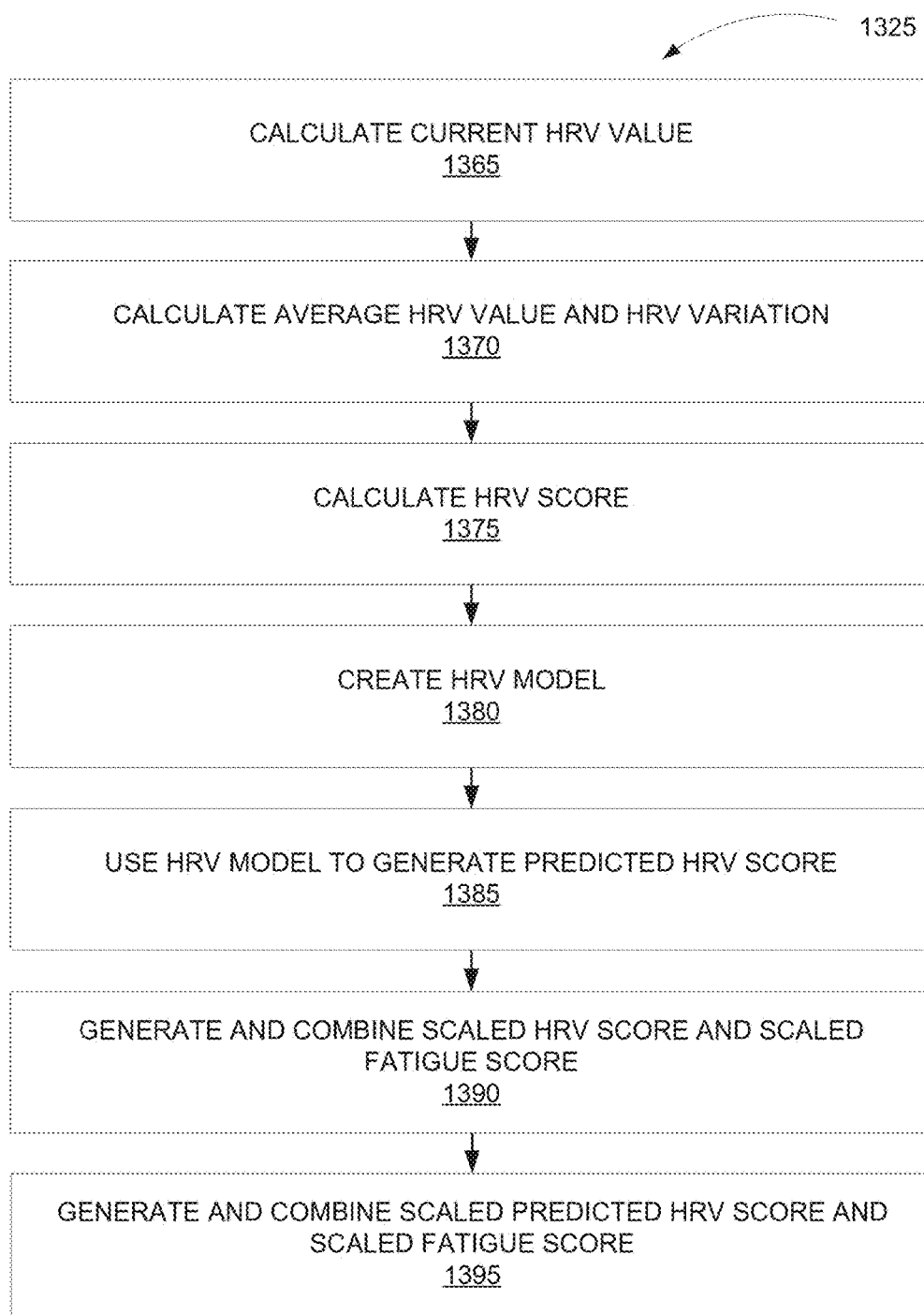
FIG. 13C is an example operational flow diagram illustrating various operations that may be performed to determine performance capacity in accordance with various embodiments described herein.

FIGS. 13A, 13B, and 13C illustrate flow charts depicting various operations of computer-implemented method 1300 and accompanying embodiments for determining performance capacity, in accordance with the present disclosure. The operations and sub-operations of method 1300 may be carried out, in some cases, by one or more of the components/elements/devices/modules of communication environment 100, computing device 120, tracking application 1015, and system 1200, described above and referenced in FIGS. 1, 8A, 8B, 9A-9F, 10A, 10B, 12A and 12B, as well as sub-components/elements/devices/modules depicted therein or described with respect thereto. In such instances, the description of method 1300 may refer to the corresponding component/element, but in any case, one of skill in the art will recognize when the corresponding component/element may be used, whether or not there is explicit reference thereto. Further, it will be appreciated that such references does not necessarily limit method 1300 to the particular component/element referred to. Thus, it will be appreciated by one of skill in the art that aspects and features described above in connection with (sub-) components/elements/devices/modules, including variations thereof, may be applied to the various operations described in connection with method 1300. Generally, method 1300 facilitates determining a user's performance capacity, including based on one or more of the user's measured biometrics and activity.

Referring now to FIG. 13A, at operation 1305, method 1300 entails measuring biometrics using a biosensor (e.g., biosensor 1210). The biosensor may be embedded in a wearable device (e.g., wearable device 1202). Measuring biometrics may include measuring a user's heart rate and calculating or estimating the user's HRV, for example. Biometrics may also include the user's temperature, blood pressure, and other physical characteristics of the user. Biometrics may be measured continuously or periodically. For example, in some cases, it may be desirable to determine the user's HRV on a daily basis. At operation 1310, method 1300 includes generating biometric data from the biometrics. This may involve circuits 1220 converting electrical signals from biosensor 1210 to a format that processor 1214 may process, store in storage 1216, and/or transmit by transmitter 1218. For example, biometric data may be generated from biometrics through analog-to-digital conversion, filtering of the biometrics, and/or encoding of the biometrics or data indicative thereof. Additionally, operation 1320 may also be performed by processor 1214 or 1224. For example, storage 1216 or 1226 may include a non-transitory computer readable medium operatively coupled to processor 1214 or 1224 and storing instructions thereon that, when executed, cause processor 1214 or 1224 to generate biometric data from the biometrics monitored by biosensor 1210, including using circuits 1220.

Method 1300 also includes, at operation 1315, monitoring activity using a motion sensor (e.g., motion sensor 1212) embedded in the wearable device (e.g., wearable device 1202). Activity may include a user's movement, such as the type of movement (e.g., running, biking, swimming, etc.) and the intensity and duration thereof, the user's location and altitude, etc. Wearable device 1202 may include additional sensors, such as a temperature sensor, altimeter, hygrometer, and the like, to measure the user's environmental conditions. Alternatively, such conditions may be determined from external sources (e.g., weather conditions or location information available via data connection to the Internet).

At operation 1320, method 1300 includes generating activity data from the activity measured by the motion sensor. In a fashion similar to operation 1310, this may entail circuits 1220 converting electrical signals from motion sensor 1212 to a format that processor 1214 may process, store in storage 1216, and/or transmit by transmitter 1218. Operation 1320 may also be performed by processor 1214 or 1224. For example, storage 1216 or 1226 may include a non-transitory computer readable medium operatively coupled to processor 1214 or 1224 and storing instructions thereon that, when executed, cause processor 1214 or 1224 to generate activity data from the activity measured by motion sensor 1212, including using circuits 1220.

At operation 1325, method 1300 involves creating a response profile. The response profile generally indicates how a user is likely to respond to a given training load or other activity. The response profile may be represented in various forms, such as, by way of example, a numerical indicator or range of values, a distribution, a descriptive indicator or expression, a color, audio or visual signals or a mix thereof, and so on, or any combination or mix of the same. Often, a user's response to a given training load will depend on many factors, including, for example, how fatigued the user is, or the user's relative amounts of activity and rest over a recent time period, fitness level, diet, environmental conditions, stress level, amount of sleep, mood, and so on. The user's HRV may act as a robust indicator of the user's capacity to exercise, need for rest, overall energy, stress levels, and other health/physical conditions. The user's HRV may be determined using biosensors, as described herein. The HRV, however, is not always available for the current day (e.g., if the user fails to enable a measurement by not wearing the wearable device, etc.). Another potentially useful indicator of the user's performance capacity is the use's recent activity levels, which may generally be referred to herein as fatigue. As mentioned above, the user's movement and hence activity may be monitored using a motion sensor and in some cases, additional hardware as described herein.

In light of the usefulness of both fatigue and HRV, and the occurrence that one or the other, or both, may in some cases not be available, the response profile is based on one or more of an HRV score, a fatigue score, a predicted HRV score, and a predicted fatigue score. As will be described in further detail, the HRV score is based on biometrics (including the user's HRV, in some cases) but is personalized to the user. Likewise, the fatigue score is based on the user's fatigue (e.g., past activity levels) but is personalized to the user. The fatigue score may be used to generate a fatigue model for the user, and the HRV score can be used to create an HRV model for the user. The fatigue model may then be used in some embodiments to generate a predicted fatigue score absent recent fatigue data, and the predicted fatigue score is based on one or more of the biometric data and the activity data. Likewise, the HRV model may be used to generate a predicted HRV score absent recent HRV measurements, and the predicted HRV score is based on one or more of the biometric data and the activity data. This will be described in detail with reference to FIGS. 13B and 13C.

Turning now to FIG. 13B, an operation flow diagram of embodiments of method 1300 and in particular of operation 1325 is provided. At operation 1330, creating the response profile (operation 1325) includes determining a fatigue value. The fatigue value is determined based on the combination of a previous fatigue value with a first difference calculated by a processor (e.g., processor 1214 or 1224). The first difference is between the previous activity value and the previous fatigue value. Further, the first difference is scaled by a fatigue decay. Equation (1), below, illustrates an example of how the fatigue value may be determined.

$$\text{fatigue }(n) = \text{fatigue }(n-m) + \frac{\text{activity value }(n-k) - \text{fatigue}(n-m)}{\text{fatigue decay}} \quad (1)$$

In equation (1), fatigue (n) represents the fatigue value at a present time/day, where n=0, while fatigue (n−m) represents the previous fatigue value from m days or units of time ago. For example, if m=1, the previous fatigue value may represent yesterday's fatigue value. Likewise, activity value (n−k) represents the previous activity value, where k=1 may correspond to yesterday's activity value. The activity value may represent a numerical count (e.g. points) based on the user's activity, including activity type, duration, intensity, and so on. If the previous fatigue value is not available, the user's average activity level may be used in equation (1) in lieu of the previous fatigue value. Fatigue decay is typically represented as a constant (e.g., 7), but may be selected from any range of numbers. In other instances, fatigue decay may be particular to the user, for example, by being derived via the HRV model that will be described herein. In short, in such instances, the fatigue decay may be based on the user's actual response to/recovery from various types of activity. Operation 1330 may be performed by processor 1214 or 1224. For example, storage 1216 or 1226 may include a non-transitory computer readable medium operatively coupled to processor 1214 or 1224 and storing instructions thereon that, when executed, cause processor 1214 or 1224 to determine the fatigue value, including by calculating the first difference, scaling the first difference by the fatigue value, and combining the scaled first difference with the previous fatigue value.

In one embodiment, a fitness value is determined. The fitness value may be determined based on the combination of a previous fitness value with a difference calculated by a processor (e.g., processor 1214 or 1224). With respect to fitness value, in example implementations, the difference is between the previous activity value and the previous fitness value. Further, the difference is scaled by a fitness decay. Equation (2), below, illustrates an example of how the fitness value may be determined.

$$\text{fitness }(n) = \text{fitness }(n-m) + \frac{\text{activity value }(n-k) - \text{fitness}(n-m)}{\text{fitness decay}} \quad (2)$$

In equation (2), fitness (n) represents the fitness value at a present time/day, where n=0, while fitness (n−m) represents the previous fitness value from m days or units of time ago. For example, if m=1, the previous fitness value may represent yesterday's fitness value. Likewise, activity value (n−k) represents the previous activity value, where k=1 may correspond to yesterday's activity value. The activity value may represent a numerical count (e.g. points) based on the user's activity, including activity type, duration, intensity, and so on. If the previous fitness value is not available, the user's average activity level may be used in equation (2) in lieu of the previous fitness value. Fitness decay is typically represented as a constant (e.g., 42), but may be selected from any range of numbers. In other instances, fitness decay may be particular to the user, for example, by being derived from characteristics of how the user recovers over time, e.g., via the HRV model that will be described herein. In short, in such instances, the fitness decay may be based on the user's actual response to/recovery from various types of activity. Operation 1330 may be performed by processor 1214 or 1224. For example, storage 1216 or 1226 may include a non-transitory computer readable medium operatively coupled to processor 1214 or 1224 and storing instructions thereon that, when executed, cause processor 1214 or 1224 to determine the fitness value, including by calculating the difference, scaling the difference by the fitness value, and combining the scaled difference with the previous fitness value.

At operation 1335, creating the response profile includes calculating an average fatigue value and a variation in the fatigue value. This calculation is based on a set of the fatigue values previous determined. The average fatigue value may be the mean, median, or mode of previously determined fatigue values (e.g., determined in previous time periods using operation 1330). In some cases, the average fatigue value includes the fatigue value determined for the present day. The variation in the fatigue value may in some cases be the standard deviation of the previously determined fatigue values determined in previous time periods, e.g., fatigue levels determined for past days. In some cases, the variation in the fatigue value includes the fatigue value determined for the present day. Operation 1335 may be performed by processor 1214 or 1224. For example, storage 1216 or 1226 may include a non-transitory computer readable medium operatively coupled to processor 1214 or 1224 and storing instructions thereon that, when executed, cause processor 1214 or 1224 to calculate the average fatigue value and the fatigue value variation.

Continuing the example, operation 1325 of method 1300 may include operation 1340, calculating the fatigue score based on a second difference. The second difference is between the average fatigue value (e.g., calculated at operation 1335) and the fatigue value (e.g., determined at operation 1330). The second difference is scaled by the variation in the fatigue value (e.g., calculated at operation 1335). Equation (3), below, illustrates an example of how the fatigue score may be calculated.

$$\text{fatigue score} = \frac{1}{\sigma} * \left\{ \frac{1}{k} \sum_{i=0}^{k} \text{fatigue value }(n-i) \right\} - \text{fatigue }(n) \quad (3)$$

In equation (3), fatigue (n–i) represents the previous fatigue value from i days or units of time ago. Thus, the summation is taken over k number of days or units of time for which previous fatigue values have been determined. The summation is then divided by k to obtain the average previous fatigue value. The starting value of i, as well as the value of k, may be changed to shift the time period over which the fatigue value is averaged. The fatigue value variation is represented in equation (3) by σ. In this manner, the fatigue score is normalized for the user, and may thus represent statistically how the user's fatigue value stacks up against the user's typical or baseline fatigue values measured over time. In this regard, the fatigue score may be normalized so as to range an upper bound to a lower bound. The upper and lower bounds may be set to be two standard deviations from the mean fatigue score. Additionally, the upper and lower bounds may be capped respectively at 100 and 0. Of course, any range of numbers may be used, depending on the circumstance. In other scenarios, the fatigue score may be scaled by an additional constant (e.g., 25, or a constant ranging from 0 to 100 or any number), and may be added to an offset (e.g., 50, or an offset ranging from 0 to 100 or any number). Operation 1340 may be performed by processor 1214 or 1224. For example, storage 1216 or 1226 may include a non-transitory computer readable medium operatively coupled to processor 1214 or 1224 and storing instructions thereon that, when executed, cause processor 1214 or 1224 to calculate the various values in equation (3) and thus they fatigue score.

Referring again to FIG. 13B, method 1300, and specifically operation 1325 thereof, in some example implementations, includes operation 1345. Operation 1345 involves maintaining, for a previous measuring period, an aggregation of the calculated fatigue scores (e.g., from operation 1340) and an aggregation of the activity data. The aggregation of the calculated fatigue scores may include fatigue scores calculated for each of a series of days that occurred during the previous measuring period. Likewise, the activity data may also correspond to activity monitored during the series of days occurring during the past measuring period. The past measuring period may be of programmable length, and may be defined in time units other than days (e.g., months, weeks, hours, etc.). The aggregation of calculated fatigue scores and the activity data may be maintained in storage 1216 and/or storage 1226, or in cloud storage (e.g., in server 1206). Operation 1345 may be performed by processor 1214 or 1224. For example, storage 1216 or 1226 may include a non-transitory computer readable medium operatively coupled to processor 1214 or 1224 and storing instructions thereon that, when executed, cause processor 1214 or 1224 to maintain the aggregation of the calculated fatigue scores and activity data.

According to various embodiments, at operation 1350, operation 1325 includes creating a fatigue model. The fatigue model is derived from a correlation of the aggregation of the calculated fatigue scores with the aggregation of the activity data. In example implementations, the fatigue model may be represented as a distribution or table of fatigue scores corresponding to ranges of activity values or other input parameters. The fatigue model may be presented to the user (e.g., via display 1030 of computing device 120). In such cases, the user may be able to tweak the model, adapt the weighting of parameters therein, and so on. Essentially, the fatigue model may be created by mapping the fatigue scores to corresponding activity data to determine the relationship between the user's activity level and the user's fatigue scores. In this manner, provided with an expected level of activity (or activity value), the fatigue model may be used to generate a predicted fatigue score, based on the correlation of previous fatigue scores to previous activity levels. This is represented at operation 1355 in FIG. 13B. The predicted fatigue score may be used to gauge what a user's response will be to a particular training load, in terms of fatigue. The fatigue model may be presented to the user (e.g., via display 1030 of computing device 120). In such cases, the user may be able to tweak the model, adapt the weighting of parameters therein, and so on. Operation 1355 may be performed by processor 1214 or 1224. For example, storage 1216 or 1226 may include a non-transitory computer readable medium operatively coupled to processor 1214 or 1224 and storing instructions thereon that, when executed, cause processor 1214 or 1224 to create the fatigue model and use the fatigue model to generate a predicted fatigue score.

FIG. 13C provides an operational flow diagram for embodiments of method 1300 and in particular in connection with operation 1325. The operations shown in FIG. 13C relate to calculating the user's HRV and an HRV score that is personalized for the user, and creating an HRV model that correlates various environmental/external conditions, such as the user's sleep, activity, rest, geographic information, and stress levels, with the user's HRV. The HRV model may be used to predict the user's HRV score in instances where the user's HRV information is not available, or in instances in which the user wishes to get a sense for the user's response to a particular training load or set of conditions.

At operation 1365, creating the response profile (operation 1325) includes calculating a current HRV value from the biometric data. The biometric data may be related to the user's heart activity, e.g., electro-cardio signals from the user's heart, and may be used to calculate HRV, as described above with reference to FIGS. 2 and 3. Operation 1365 may be performed by processor 1214 or 1224. For example, storage 1216 or 1226 may include a non-transitory computer readable medium operatively coupled to processor 1214 or 1224 and storing instructions thereon that, when executed, cause processor 1214 or 1224 to calculate the HRV value from the biometric data.

At operation 1370, creating the response profile includes calculating an average HRV value and an HRV variation. This may be done in a fashion similar to operation 1335. Here, the calculation is based on an a set of HRV values previously calculated based on the biometric data. The average HRV value may be the mean, median, or mode of previously calculated HRV values (e.g., the current HRV values calculated for previous time periods using operation 1365). In some cases, the average HRV value includes the HRV value determined for the present day. The variation in the HRV value, or the HRV variation, may in some cases be the standard deviation of the previously calculated HRV values determined in previous time periods, e.g., HRV values determined for past days. In some cases, the HRV variation includes the HRV value determined for the present day. Operation 1370 may be performed by processor 1214 or 1224. For example, storage 1216 or 1226 may include a non-transitory computer readable medium operatively coupled to processor 1214 or 1224 and storing instructions thereon that, when executed, cause processor 1214 or 1224 to calculate the average HRV value and to calculate the variation in the HRV value.

As illustrated in FIG. 13C, operation 1325 may also include calculating an HRV score, at operation 1375. The HRV score is calculated based on a difference between the average HRV value (e.g., calculated at operation 1370) and the current HRV value (e.g., calculated at operation 1365).

Moreover, the difference is scaled by the HRV variation (e.g., calculated at operation 1370). Equation (4), below, illustrates an example of how the HRV score may be calculated.

$$HRV\ score = \frac{1}{\sigma} * \frac{1}{k} * \left\{\sum_{i=0}^{k} HRV\ value\ (n-i)\right\} - HRV\ (n) \quad (4)$$

In equation (4), HRV value (n−i) represents a previously calculated HRV value from i days or units of time ago. Thus, the summation is taken over k number of days or units of time for which previous fatigue values have been determined. The summation is then divided by k to obtain the average of the previously calculated HRV values. The starting value of i, as well as the value of k, may be changed to shift the time period over which the HRV value is averaged. The HRV variation is represented in equation (4) by $\sigma$. In this manner, the HRV score is normalized for the user, and may thus represent statistically how the user's current HRV value stacks up against the user's typical or baseline HRV values measured over time. In this regard, the HRV score may be normalized so as to range between an upper bound to a lower bound. The upper and lower bounds may be set to be two standard deviations from the mean HRV score. Additionally, the upper and lower bounds may be capped respectively at 100 and 0. Of course, any range of numbers may be used, depending on the circumstance. In other scenarios, the HRV score may be scaled by an additional constants, and may be added to an offset. Operation 1375 may be performed by processor 1214 or 1224. For example, storage 1216 or 1226 may include a non-transitory computer readable medium operatively coupled to processor 1214 or 1224 and storing instructions thereon that, when executed, cause processor 1214 or 1224 to calculate the difference and scale the same by the HRV variation.

According to various embodiments, at operation 1380, operation 1325 includes creating an HRV model. The HRV model is based on a correlation of calculated HRV scores, which may be aggregated over time and stored with the activity data, which likewise may be aggregated and stored. Essentially, the HRV model may be created by mapping the HRV scores to corresponding activity data to determine the relationship between the user's activity level and the user's fatigue scores. In some cases, the HRV score may further be mapped to aggregated biometric data other than HRV (e.g., the user's temperature and so on), or to aggregated environmental data indicative of environmental conditions described above. In this manner, provided with an expected level of activity (or activity value) or expected environmental conditions or biometrics, the HRV model may be used to generate a predicted HRV score. This is represented at operation 1385 in FIG. 13C.

The HRV model may be used to gauge what a user's response will be to a particular training load and/or environmental conditions and/or biometrics, in terms of HRV. In example implementations, the HRV model may be represented as a distribution or table of HRV scores corresponding to ranges of activity values or other input parameters (e.g., biometrics or environmental conditions). The HRV model may be presented to the user (e.g., via display 1030 of computing device 120). In such cases, the user may be able to tweak the model, adapt the weighting of parameters therein, and so on. Operations 1380 and 1385 may be performed by processor 1214 or 1224. For example, storage 1216 or 1226 may include a non-transitory computer readable medium operatively coupled to processor 1214 or 1224 and storing instructions thereon that, when executed, cause processor 1214 or 1224 to create the HRV model and use the HRV model to generate the predicted HRV score based on the activity data.

Referring again to FIG. 13C, embodiments of operation 1325 include, at operation 1390, generating a scaled HRV score from the HRV score, and generating a scaled fatigue score from the fatigue score. The HRV score and the fatigue score may be scaled by respective scaling factors. For example, the scaling factors may be fractions less than 1, thus decreasing the value of the HRV score or fatigue score, or may be greater than 1 in order to increase the value of the scores. In other cases, the scaling factors may be negative. Referring again to operation 1390, the scaled HRV score and the scaled fatigue score may be combined. As shown below in equation (5), the respective scaling factors may be used to determine the mix that the HRV score and the fatigue score contribute to the combination. The combination, in one instance, may represent the response profile.

$$\text{response profile} = \alpha * \text{fatigue score} + \beta * \text{HRV score} \quad (5)$$

In equation (5), $\alpha$ corresponds to the scaling factor for the fatigue score, and $\beta$ corresponds to the scaling factor for the HRV score. In some cases, a may be set to zero, such that only the HRV score contributes to the response profile. Typically, $\beta$ will be set to 1 in such cases. In other cases, $\beta$ may be set to zero, such that only the fatigue score contributes to the response profile. Typically, $\alpha$ will be set to 1 in such cases. In one embodiment $\alpha$ and $\beta$ are both set to 0.5, such that the fatigue score and the HRV score contribute equally to the response profile. In another embodiment, $\beta$ is set to 0.75 and $\alpha$ is set to 0.25, such that the HRV score contributes more to the response profile. This weighting may emphasize the user's holistic response to all environmental and other inputs besides, as captured by the user's tailored HRV score, as opposed to emphasizing contribution from the user's activity, as captured by the fatigue score.

At operation 1395, operation 1325 of method 1300 includes generating a scaled predicted HRV score from the predicted HRV score, and generating a scaled fatigue score from the fatigue score. The scaled predicted HRV score may be scaled by a scaling factor, in a fashion similar to that described above in connection with operation 1390. Referring again to operation 1395, the scaled predicted HRV score and the scaled fatigue score may be combined. As shown below in equation (6), the respective scaling factors may be used to determine the mix that the predicted HRV score and the fatigue score contribute to the combination. The combination, in one instance, may represent the response profile.

$$\text{response profile} = \alpha * \text{fatigue score} + \gamma * \text{predicted HRV score} \quad (6)$$

In equation (6), $\alpha$ corresponds to the scaling factor for the fatigue score, and $\gamma$ corresponds to the scaling factor for the predicted HRV score. In some cases, $\alpha$ may be set to zero, such that only the predicted HRV score contributes to the response profile. Typically, $\gamma$ will be set to 1 in such cases. In other cases, $\gamma$ may be set to zero, such that only the fatigue score contributes to the response profile. Typically, $\alpha$ will be set to 1 in such cases. For example, such cases may occur where it is desired for the response profile to focus only on the user's activity and to diminish the user's response to other factors such as, by way of illustration, the user's physical response to activity, which may generally be accounted for using HRV. Additionally, $\gamma$ may be set to zero if there is simply no HRV information available (e.g., if the user has never measured HRV). In one embodiment α and γ are both set to 0.5, such that the fatigue score and the predicted HRV score contribute equally to the response profile. In another embodiments, α and γ may be varied or programmed, such that the predicted HRV score or the fatigue score contributes more to the response profile. The predicted fatigue score may be substituted in equations (5) or (6) and scaled and combined with either the HRV score or the predicted HRV score as described above with regard to the fatigue score.

Figure 14:
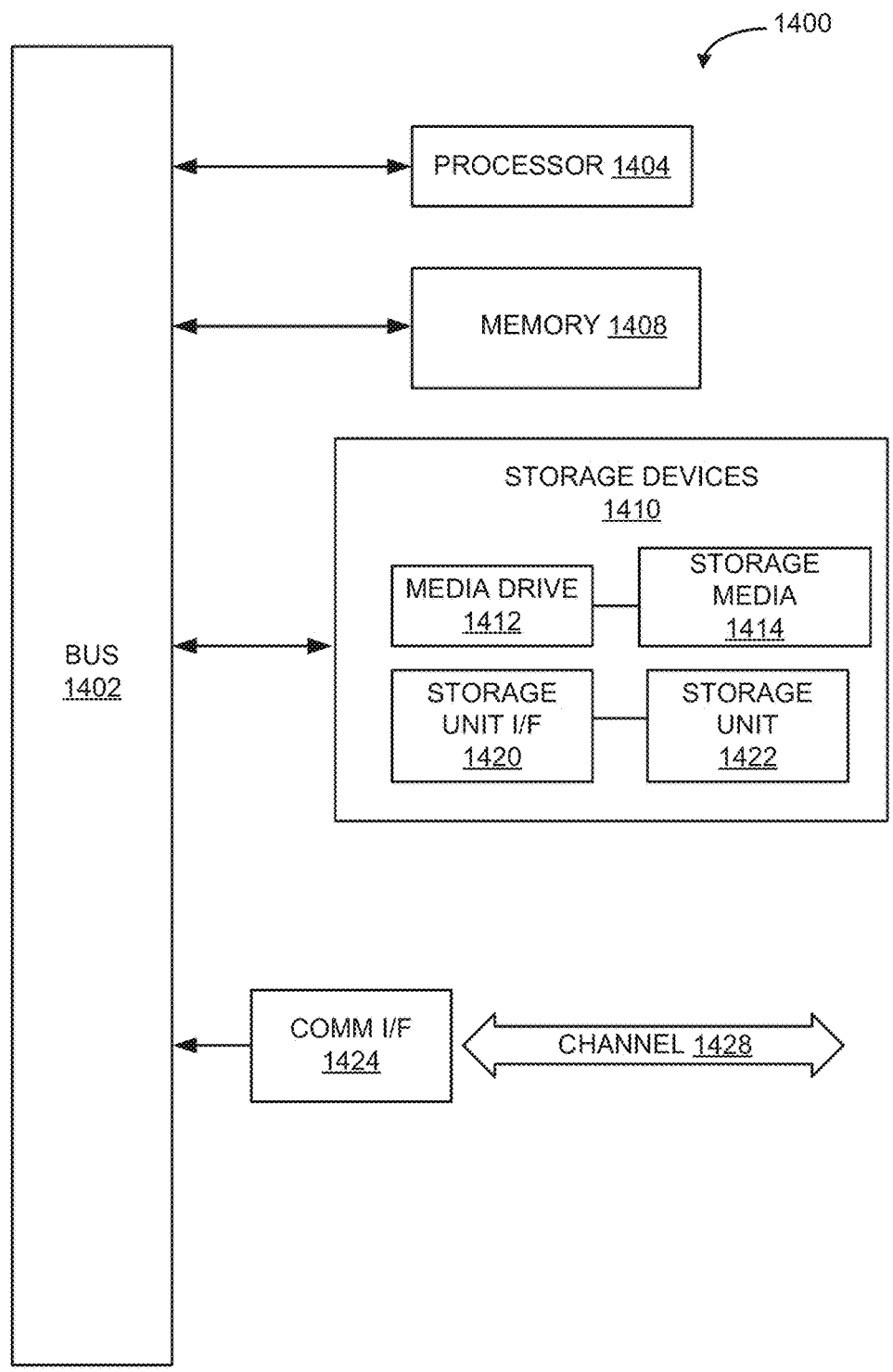
FIG. 14 illustrates an example computing module that may be used to implement features of various embodiments of the disclosure.

FIG. 14 illustrates example computing module 1400, which may in some instances include a processor/controller resident on a computer system (e.g., computing device 120 or wearable device 1202). Computing module 1400 may be used to implement various features and/or functionality of embodiments of the systems and methods disclosed herein. With regard to the above-described embodiments of computing module 1400, computing device 120, and wearable device 1202, one of skill in the art will appreciate additional variations and details regarding the functionality of the embodiments, as set forth herein in the context of systems and method described with reference to FIGS. 1 through 14. In this connection, it will also be appreciated by one of skill in the art that features and aspects of the various embodiments (e.g., systems) described herein may be implemented with respected to other embodiments (e.g., methods) described herein without departing from the spirit of the disclosure.

As used herein, the term module may describe a given unit of functionality that may be performed in accordance with one or more embodiments of the present application. As used herein, a module may be implemented utilizing any form of hardware, software, or a combination thereof. For example, one or more processors, controllers, ASICs, PLAs, PALs, CPLDs, FPGAs, logical components, software routines or other mechanisms may be implemented to make up a module. In implementation, the various modules described herein may be implemented as discrete modules or the functions and features described may be shared in part or in total among one or more modules. In other words, as would be apparent to one of ordinary skill in the art after reading this description, the various features and functionality described herein may be implemented in any given application and may be implemented in one or more separate or shared modules in various combinations and permutations. Even though various features or elements of functionality may be individually described or claimed as separate modules, one of ordinary skill in the art will understand that these features and functionality may be shared among one or more common software and hardware elements, and such description shall not require or imply that separate hardware or software components are used to implement such features or functionality.

Where components or modules of the application are implemented in whole or in part using software, in one embodiment, these software elements may be implemented to operate with a computing or processing module capable of carrying out the functionality described with respect thereto. One such example computing module is shown in FIG. 14. Various embodiments are described in terms of example computing module 1400. After reading this description, it will become apparent to a person skilled in the relevant art how to implement the application using other computing modules or architectures.

Referring now to FIG. 14, computing module 1400 may represent, for example, computing or processing capabilities found within mainframes, supercomputers, workstations or servers; desktop, laptop, notebook, or tablet computers; hand-held computing devices (tablets, PDA's, smartphones, cell phones, palmtops, etc.); or the like, depending on the application and/or environment for which computing module 1400 is specifically purposed.

Computing module 1400 may include, for example, one or more processors, controllers, control modules, or other processing devices, such as a processor 1404. Processor 604 may be implemented using a special-purpose processing engine such as, for example, a microprocessor, controller, or other control logic. In the illustrated example, processor 604 is connected to bus 1402, although any communication medium may be used to facilitate interaction with other components of computing module 1400 or to communicate externally.

Computing module 1400 may also include one or more memory modules, simply referred to herein as main memory 1408. For example, random access memory (RAM) or other dynamic memory may be used for storing information and instructions to be executed by processor 1404. Main memory 1408 may also be used for storing temporary variables or other intermediate information during execution of instructions to be executed by processor 1404. Computing module 1400 may likewise include a read only memory (ROM) or other static storage device coupled to bus 1402 for storing static information and instructions for processor 1404.

Computing module 1400 may also include one or more various forms of information storage devices 1410, which may include, for example, media drive 1412 and storage unit interface 1420. Media drive 1412 may include a drive or other mechanism to support fixed or removable storage media 1414. For example, a hard disk drive, a floppy disk drive, a magnetic tape drive, an optical disk drive, a CD or DVD drive (R or RW), or other removable or fixed media drive may be provided. Accordingly, removable storage media 1414 may include, for example, a hard disk, a floppy disk, magnetic tape, cartridge, optical disk, a CD or DVD, or other fixed or removable medium that is read by, written to or accessed by media drive 1412. As these examples illustrate, removable storage media 1414 may include a computer usable storage medium having stored therein computer software or data.

In alternative embodiments, information storage devices 1410 may include other similar instrumentalities for allowing computer programs or other instructions or data to be loaded into computing module 1400. Such instrumentalities may include, for example, fixed or removable storage unit 1422 and storage unit interface 1420. Examples of such removable storage units 1422 and storage unit interfaces 1420 may include a program cartridge and cartridge interface, a removable memory (for example, a flash memory or other removable memory module) and memory slot, a PCMCIA slot and card, and other fixed or removable storage units 1422 and storage unit interfaces 1420 that allow software and data to be transferred from removable storage unit 1422 to computing module 1400.

Computing module 1400 may also include a communications interface 1424. Communications interface 1424 may be used to allow software and data to be transferred between computing module 1400 and external devices. Examples of communications interface 1424 include a modem or soft-modem, a network interface (such as an Ethernet, network interface card, WiMedia, IEEE 802.XX or other interface), a communications port (such as for example, a USB port, IR port, RS232 port Bluetooth® interface, or other port), or other communications interface. Software and data transferred via communications interface 1424 may typically be carried on signals, which may be electronic, electromagnetic (which includes optical) or other signals capable of being exchanged by a given communications interface 1424. These signals may be provided to communications interface 1424 via channel 1428. Channel 1428 may carry signals and may be implemented using a wired or wireless communication medium. Some non-limiting examples of channel 1428 include a phone line, a cellular link, an RF link, an optical link, a network interface, a local or wide area network, and other wired or wireless communications channels.

In this document, the terms "computer program medium" and "computer usable medium" are used to generally refer to transitory or non-transitory media such as, for example, main memory 1408, storage unit interface 1420, removable storage media 1414, and channel 1428. These and other various forms of computer program media or computer usable media may be involved in carrying one or more sequences of one or more instructions to a processing device for execution. Such instructions embodied on the medium, are generally referred to as "computer program code" or a "computer program product" (which may be grouped in the form of computer programs or other groupings). When executed, such instructions may enable the computing module 1400 or a processor to perform features or functions of the present application as discussed herein.

Various embodiments have been described with reference to specific example features thereof. It will, however, be evident that various modifications and changes may be made thereto without departing from the broader spirit and scope of the various embodiments as set forth in the appended claims. The specification and figures are, accordingly, to be regarded in an illustrative rather than a restrictive sense.

Although described above in terms of various example embodiments and implementations, it should be understood that the various features, aspects and functionality described in one or more of the individual embodiments are not limited in their applicability to the particular embodiment with which they are described, but instead may be applied, alone or in various combinations, to one or more of the other embodiments of the present application, whether or not such embodiments are described and whether or not such features are presented as being a part of a described embodiment. Thus, the breadth and scope of the present application should not be limited by any of the above-described example embodiments.

Terms and phrases used in the present application, and variations thereof, unless otherwise expressly stated, should be construed as open ended as opposed to limiting. As examples of the foregoing: the term "including" should be read as meaning "including, without limitation" or the like; the term "example" is used to provide illustrative instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, may be combined in a single package or separately maintained and may further be distributed in multiple groupings or packages or across multiple locations.

Additionally, the various embodiments set forth herein are described in terms of example block diagrams, flow charts, and other illustrations. As will become apparent to one of ordinary skill in the art after reading this document, the illustrated embodiments and their various alternatives may be implemented without confinement to the illustrated examples. For example, block diagrams and their accompanying description should not be construed as mandating a particular architecture or configuration.

What is claimed is:

1. A system for determining performance capacity, the system comprising:
   a wearable device, comprising:
      a biosensor configured to measure biometrics including a heart rate of a user; and
      a motion sensor configured to monitor activity of the user;
   a processor coupled to the biosensor and the motion sensor, the processor configured to process electronic signals generated by the biosensor and the motion sensor; and
   a non-transitory computer-readable medium operatively coupled to the processor and storing instructions that, when executed, cause the processor to:
      generate biometric data including a heart rate variability (HRV) of the user from the biometrics of the user measured by the biosensor;
      generate activity data from the activity of the user monitored by the motion sensor;
      generate a predicted HRV score of the user when a signal for determining the heart rate of the user from the biosensor is unavailable, wherein the predicted HRV score is based on the generated biometric data and the generated activity data;
      generate a fatigue score from the generated activity data;
      create a response profile for the user based on the fatigue score and the predicted HRV score; and
      provide the response profile to the user, wherein the response profile indicates a capacity of the user to perform an activity.

2. The system of claim 1, wherein
   the wearable device comprises one of earphones and a band, and
   the biosensor comprises finger and wrist biosensors or an optical heartrate sensor.

3. The system of claim 1, wherein the non-transitory computer-readable medium further stores instructions that, when executed, cause the processor to:
   determine a fatigue value based on the combination of a previous fatigue value with a first difference calculated by the processor, the first difference being between a previous activity value and the previous fatigue value, the first difference being scaled by a fatigue decay, the previous activity value being derived from the activity data;

calculate an average fatigue value based on a set of the fatigue values previously determined;

calculate a fatigue value variation based on the set of the fatigue values previously determined;

calculate the fatigue score based on a second difference calculated by the processor, the second difference being between the average fatigue value and the fatigue value, the second difference being scaled by the fatigue value variation; and provide the fatigue value to the user.

4. The system of claim 3, wherein the non-transitory computer-readable medium further stores instructions that, when executed, cause the processor to:

maintain, for a previous measuring period, an aggregation of the calculated fatigue scores and an aggregation of the activity data;

create a fatigue model derived from a correlation of the aggregation of calculated fatigue scores with the aggregation of the activity data; and use the fatigue model to generate the predicted fatigue score based on the activity data.

5. The system of claim 1, further comprising circuits that receive and process electrical signals from the biosensor, wherein the non-transitory computer-readable medium further stores instructions that, when executed, cause the processor to:

generate the biometric data based on the electrical signals as processed by the circuits;

calculate a current HRV value from the biometric data; and calculate an average HRV value based on a set of HRV values previously calculated;

calculate variation in the HRV value based on the set of the HRV values previously calculated; and calculate the HRV score based on a difference between the average HRV value and the current HRV value, the difference being scaled by the variation in the HRV value.

6. The system of claim 5, wherein the non-transitory computer-readable medium further stores instructions that, when executed, cause the processor to:

maintain, for a previous measuring period, an aggregation of the calculated HRV scores and an aggregation of the activity data;

create an HRV model derived from a correlation of the aggregation of the calculated HRV scores with the aggregation of the activity data; and use the HRV model to generate the predicted HRV score based on the activity data.

7. The system of claim 1, wherein the wearable device comprises earphones, wherein the earphones are used to provide the response profile to the user in an audio format.

8. The system of claim 1, wherein the wearable device comprises a band, wherein the band is used to provide the response profile to the user in a visual format.

9. The system of claim 1, wherein the predicted HRV score of the user is generated when a signal for determining the heart rate of the user from the biosensor is unavailable for at least a period of 24 hours.

* * * * *